United States Patent
Shelton, IV

(10) Patent No.: US 12,011,217 B2
(45) Date of Patent: Jun. 18, 2024

(54) ELECTROSURGICAL INSTRUMENT WITH MODULAR COMPONENT CONTACT MONITORING

(71) Applicant: Cilag GmbH International, Zug (CH)

(72) Inventor: Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 268 days.

(21) Appl. No.: 17/136,158

(22) Filed: Dec. 29, 2020

(65) Prior Publication Data

US 2022/0202488 A1 Jun. 30, 2022

(51) Int. Cl.
*A61B 18/16* (2006.01)
*A61B 18/00* (2006.01)
(Continued)

(52) U.S. Cl.
CPC .......... *A61B 18/16* (2013.01); *A61B 18/1206* (2013.01); *A61B 34/37* (2016.02); *A61B 2018/00083* (2013.01); *A61B 2018/00178* (2013.01); *A61B 2018/00601* (2013.01); *A61B 2018/0063* (2013.01);
(Continued)

(58) Field of Classification Search
CPC ..... A61B 18/16; A61B 34/37; A61B 18/1206; A61B 2018/00083; A61B 2018/00178; A61B 2018/00601; A61B 2018/0063; A61B 2018/00666; A61B 2018/00702; A61B 2018/0072; A61B 2018/00755; A61B 2018/00767; A61B 2018/1253
See application file for complete search history.

(56) References Cited

U.S. PATENT DOCUMENTS

| | | |
|---|---|---|
| 4,184,492 A | 1/1980 | Meinke et al. |
| 5,312,401 A | 5/1994 | Newton et al. |

(Continued)

FOREIGN PATENT DOCUMENTS

| | | |
|---|---|---|
| EP | 2926752 A2 | 10/2015 |
| EP | 3417797 A1 | 12/2018 |

(Continued)

OTHER PUBLICATIONS

U.S. Appl. No. 17/136,137.

(Continued)

*Primary Examiner* — Linda C Dvorak
*Assistant Examiner* — Abigail Bock
(74) *Attorney, Agent, or Firm* — Frost Brown Todd LLP

(57) ABSTRACT

An apparatus includes a shaft assembly, an end effector, a control module, a first electrical connector, and a plurality of nonconductive structures. The first electrical connector is operatively coupled with the control module and includes a first plurality of electrical contacts. At least one electrical contact of the first plurality of electrical contacts is configured to transfer a power output from the control module to a second plurality of electrical contacts of a second electrical connector while the first and second electrical connectors are coupled. The nonconductive structures are disposed adjacent each of the plurality of first electrical contacts. The nonconductive structures are configured to prevent a signal interference between each electrical contact of the first plurality of electrical contacts.

17 Claims, 12 Drawing Sheets

(51) Int. Cl.
*A61B 18/12* (2006.01)
*A61B 34/37* (2016.01)

(52) U.S. Cl.
CPC ............ *A61B 2018/00666* (2013.01); *A61B 2018/00702* (2013.01); *A61B 2018/0072* (2013.01); *A61B 2018/00755* (2013.01); *A61B 2018/00767* (2013.01); *A61B 2018/1253* (2013.01)

(56) References Cited

U.S. PATENT DOCUMENTS

| | | | |
|---|---|---|---|
| 7,070,420 B1 * | 7/2006 | Wakefield | H01R 13/2414 |
| | | | 439/66 |
| 7,354,440 B2 | 4/2008 | Truckai et al. | |
| 7,381,209 B2 | 6/2008 | Truckai et al. | |
| 7,762,958 B1 | 7/2010 | Webler | |
| 8,663,220 B2 * | 3/2014 | Wiener | A61N 7/00 |
| | | | 606/41 |
| 8,820,605 B2 | 9/2014 | Shelton, IV | |
| 9,125,662 B2 | 9/2015 | Shelton, IV | |
| 9,314,308 B2 | 4/2016 | Parihar et al. | |
| 9,949,785 B2 | 4/2018 | Price et al. | |
| 10,090,616 B1 | 10/2018 | Leimbach et al. | |
| 10,624,709 B2 | 4/2020 | Remm | |
| 10,639,038 B2 | 5/2020 | Scott et al. | |
| 10,813,640 B2 | 10/2020 | Adams et al. | |
| 10,835,307 B2 | 11/2020 | Shelton, IV et al. | |
| 10,842,523 B2 | 11/2020 | Shelton, IV et al. | |
| 2002/0128643 A1 | 9/2002 | Simpson et al. | |
| 2004/0206365 A1 | 10/2004 | Knowlton | |
| 2006/0041251 A1 | 2/2006 | Odell et al. | |
| 2006/0041252 A1 | 2/2006 | Odell et al. | |
| 2006/0079874 A1 | 4/2006 | Faller et al. | |
| 2007/0049919 A1 | 3/2007 | Lee, Jr. et al. | |
| 2007/0191713 A1 | 8/2007 | Eichmann et al. | |
| 2008/0200940 A1 | 8/2008 | Eichmann et al. | |
| 2009/0036884 A1 | 2/2009 | Gregg et al. | |
| 2010/0042097 A1 | 2/2010 | Newton et al. | |
| 2011/0034910 A1 | 2/2011 | Ross et al. | |
| 2012/0292367 A1 | 11/2012 | Morgan et al. | |
| 2013/0123783 A1 | 5/2013 | Marczyk et al. | |
| 2014/0249557 A1 | 9/2014 | Koch, Jr. et al. | |
| 2015/0313628 A1 | 11/2015 | Allen, IV | |
| 2015/0320481 A1 | 11/2015 | Cosman, Jr. et al. | |
| 2016/0143685 A1 | 5/2016 | Friedrichs | |
| 2016/0192980 A1 | 7/2016 | Newton et al. | |
| 2016/0296268 A1 | 10/2016 | Gee et al. | |
| 2017/0202591 A1 | 7/2017 | Shelton, IV et al. | |
| 2017/0202605 A1 | 7/2017 | Shelton, IV et al. | |
| 2017/0202608 A1 | 7/2017 | Shelton, IV et al. | |
| 2018/0012719 A1 * | 1/2018 | Houbre | H01H 71/125 |
| 2018/0078170 A1 | 3/2018 | Panescu et al. | |
| 2018/0132850 A1 | 5/2018 | Leimbach et al. | |
| 2018/0333185 A1 | 11/2018 | Asher et al. | |
| 2019/0142492 A1 | 5/2019 | Kollmann et al. | |
| 2019/0189903 A1 * | 6/2019 | Benedict | H10N 30/50 |
| 2019/0201047 A1 | 7/2019 | Yates et al. | |
| 2019/0201075 A1 | 7/2019 | Shelton, IV et al. | |
| 2019/0201077 A1 | 7/2019 | Yates et al. | |
| 2019/0247680 A1 | 8/2019 | Mayer et al. | |
| 2019/0290269 A1 | 9/2019 | Shelton, IV et al. | |
| 2019/0290273 A1 | 9/2019 | Shelton, IV et al. | |
| 2019/0290308 A1 * | 9/2019 | Worthington | H01R 13/2407 |
| 2020/0069365 A1 | 3/2020 | Harley et al. | |
| 2020/0078075 A1 | 3/2020 | Katsuragi | |
| 2020/0384502 A1 | 12/2020 | Downey et al. | |
| 2021/0059709 A1 | 3/2021 | Black et al. | |
| 2022/0202470 A1 | 6/2022 | Shelton, IV | |
| 2022/0202474 A1 | 6/2022 | Shelton, IV et al. | |
| 2022/0202475 A1 | 6/2022 | Shelton, IV et al. | |
| 2022/0202476 A1 | 6/2022 | Shelton, IV | |
| 2022/0202487 A1 | 6/2022 | Shelton, IV et al. | |

FOREIGN PATENT DOCUMENTS

| | | |
|---|---|---|
| EP | 3420918 A1 | 1/2019 |
| EP | 3461447 A1 | 4/2019 |
| EP | 3479787 A1 | 5/2019 |
| EP | 3542733 A1 | 9/2019 |
| WO | WO 1992/008417 A1 | 5/1992 |
| WO | WO 2018/165425 A1 | 9/2018 |
| WO | WO 2019/130111 A1 | 7/2019 |
| WO | WO 2020/051462 A1 | 3/2020 |

OTHER PUBLICATIONS

U.S. Appl. No. 17/136,139.
U.S. Appl. No. 17/136,141.
U.S. Appl. No. 17/136,145.
U.S. Appl. No. 17/136,154.
U.S. Appl. No. 17/136,137, entitled "Filter for Monopolar Surgical Instrument Energy Path," filed Dec. 29, 2020.
U.S. Appl. No. 17/136,139, entitled "Electrosurgical Instrument System with Parasitic Energy Loss Monitor," filed Dec. 29, 2020.
U.S. Appl. No. 17/136,141, entitled "Energized Surgical Instrument System with Multi-Generator Output Monitoring," filed Dec. 29, 2020.
U.S. Appl. No. 17/136,145, entitled "Electrosurgical Instrument with Shaft Voltage Monitor," filed Dec. 29, 2020.
U.S. Appl. No. 17/136,154, entitled "Electrosurgical Instrument with Electrical Resistance Monitor at Rotary Coupling," filed Dec. 29, 2020.
International Search Report and Written Opinion dated May 17, 2022, for International Application No. PCT/IB2021/062411, 20 pages.
International Search Report and Written Opinion dated Mar. 22, 2022, for International Application No. PCT/IB2021/062413, 13 pages.
International Search Report and Written Opinion dated Mar. 24, 2022, for International Application No. PCT/IB2021/062414, 17 pages.
International Search Report and Written Opinion dated Mar. 24, 2022, for International Application No. PCT/IB2021/062416, 16 pages.
International Search Report and Written Opinion dated Mar. 30, 2022, for International Application No. PCT/IB2021/062417, 17 pages.
International Search Report and Written Opinion dated Apr. 7, 2022, for International Application No. PCT/IB2021/062418, 13 pages.

* cited by examiner

ELECTROSURGICAL INSTRUMENT WITH MODULAR COMPONENT CONTACT MONITORING

BACKGROUND

A variety of ultrasonic surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. Examples of ultrasonic surgical instruments and related concepts are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein, in its entirety; U.S. Pub. No. 2007/0191713, entitled "Ultrasonic Device for Cutting and Coagulating," published Aug. 16, 2007, now abandoned, the disclosure of which is incorporated by reference herein, in its entirety; and U.S. Pub. No. 2008/0200940, entitled "Ultrasonic Device for Cutting and Coagulating," published Aug. 21, 2008, now abandoned, the disclosure of which is incorporated by reference herein, in its entirety.

Some instruments are operable to seal tissue by applying radiofrequency (RF) electrosurgical energy to the tissue. Examples of such devices and related concepts are disclosed in U.S. Pat. No. 7,354,440, entitled "Electrosurgical Instrument and Method of Use," issued Apr. 8, 2008, the disclosure of which is incorporated by reference herein, in its entirety; U.S. Pat. No. 7,381,209, entitled "Electrosurgical Instrument," issued Jun. 3, 2008, the disclosure of which is incorporated by reference herein, in its entirety.

Some instruments are capable of applying both ultrasonic energy and RF electrosurgical energy to tissue. Examples of such instruments are described in U.S. Pat. No. 9,949,785, entitled "Ultrasonic Surgical Instrument with Electrosurgical Feature," issued Apr. 24, 2018, the disclosure of which is incorporated by reference herein, in its entirety; and U.S. Pat. No. 8,663,220, entitled "Ultrasonic Electrosurgical Instruments," issued Mar. 4, 2014, the disclosure of which is incorporated by reference herein, in its entirety.

In some scenarios, it may be preferable to have surgical instruments grasped and manipulated directly by the hand or hands of one or more human operators. In addition, or as an alternative, it may be preferable to have surgical instruments controlled via a robotic surgical system. Examples of robotic surgical systems and associated instrumentation are disclosed in U.S. Pat. No. 10,624,709, entitled "Robotic Surgical Tool with Manual Release Lever," published on Apr. 21, 2020, the disclosure of which is incorporated by reference herein, in its entirety; U.S. Pat. No. 9,314,308, entitled "Robotic Ultrasonic Surgical Device With Articulating End Effector," issued on Apr. 19, 2016, the disclosure of which is incorporated by reference herein, in its entirety; U.S. Pat. No. 9,125,662, entitled "Multi-Axis Articulating and Rotating Surgical Tools," issued Sep. 8, 2015, the disclosure of which is incorporated by reference herein, in its entirety; U.S. Pat. No. 8,820,605, entitled "Robotically-Controlled Surgical Instruments," issued Sep. 2, 2014, the disclosure of which is incorporated by reference herein, in its entirety; U.S. Pub. No. 2019/0201077, entitled "Interruption of Energy Due to Inadvertent Capacitive Coupling," published Jul. 4, 2019, issued as U.S. Pat. No. 11,291,495 on Apr. 5, 2022, the disclosure of which is incorporated by reference herein, in its entirety; U.S. Pub. No. 2012/0292367, entitled "Robotically-Controlled End Effector," published on Nov. 11, 2012, now abandoned, the disclosure of which is incorporated by reference herein, in its entirety; and U.S. patent application Ser. No. 16/556,661, entitled "Ultrasonic Surgical Instrument with a Multi-Planar Articulating Shaft Assembly," filed on Aug. 30, 2019, issued as U.S. Pat. No. 11,690,642 on Jul. 4, 2023, the disclosure of which is incorporated by reference herein, in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
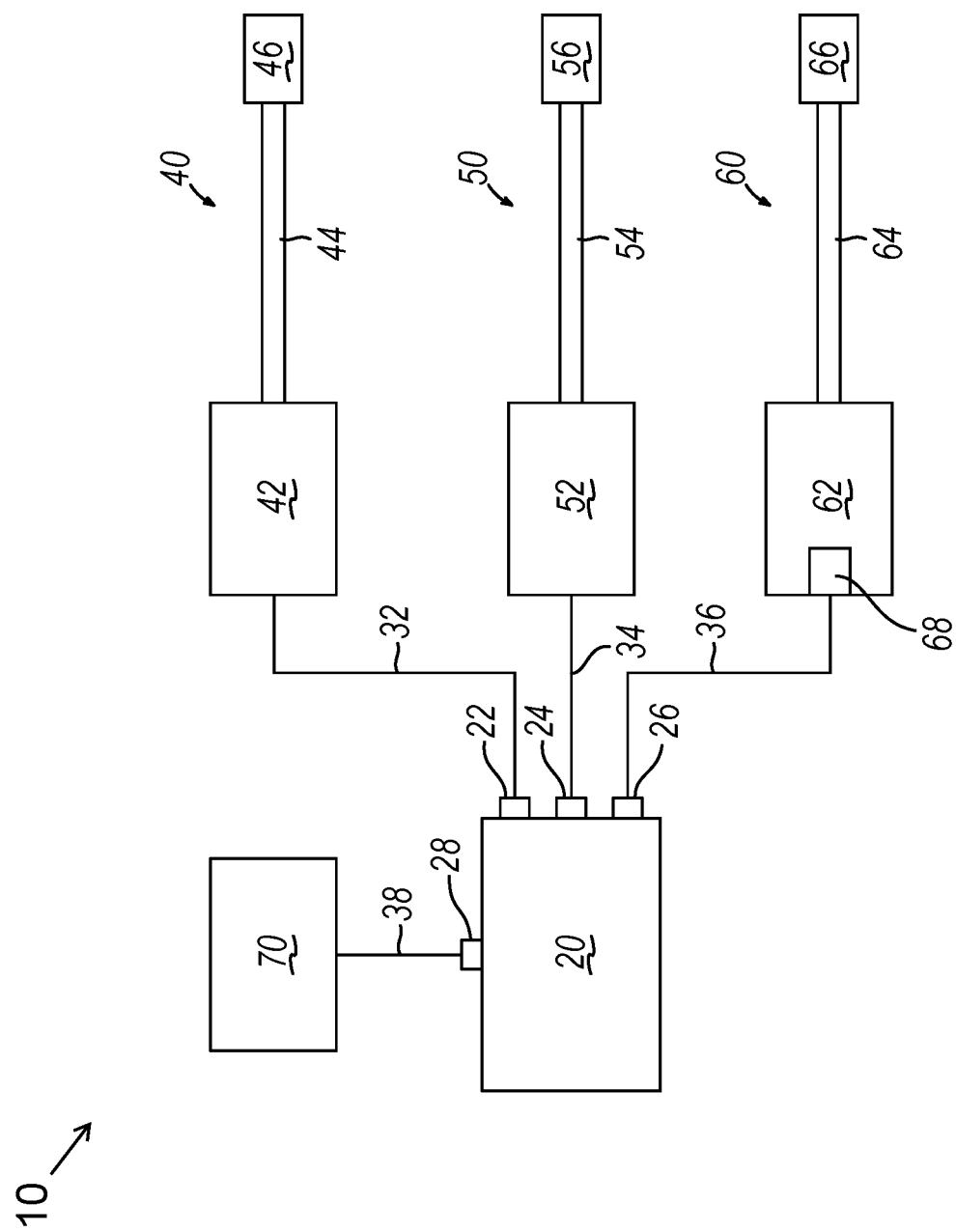
FIG. 1 depicts a schematic view of an example of a robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. In addition, the terms "upper," "lower," "top," "bottom," "above," and "below," are used with respect to the examples and associated figures and are not intended to unnecessarily limit the invention described herein.

I. Example of a Robotic Surgical System

As noted above, in some surgical procedures, it may be desirable to utilize a robotically controlled surgical system. Such a robotically controlled surgical system may include one or more surgical instruments that are controlled and driven robotically via one or more users that are either in the same operating room or remote from the operating room. FIG. 1 illustrates on example of various components that may be incorporated into a robotic surgical system (10). System (10) of this example includes a console (20), a monopolar RF electrosurgical instrument (40), a bipolar RF electrosurgical instrument (50), and an ultrasonic surgical instrument (60). While FIG. 1 shows all three instruments (40, 50, 60) coupled with console (20) at the same time, there may be usage scenarios where only one or two of instruments (40, 50, 60) coupled with console (20) at the same time. In addition, there may be usage scenarios where various other instruments are coupled with console (20) in addition, or as an alternative to, one or more of instruments (40, 50, 60) being coupled with console (20).

Monopolar RF electrosurgical instrument (40) of the present example includes a body (42), a shaft (44) extending distally from body (42), and an end effector (46) at the distal end of shaft (44). Body (42) is configured to couple with a robotic arm (not shown in FIG. 1) of system (10), such that the robotic arm is operable to position and orient monopolar RF electrosurgical instrument (40) in relation to a patient. In versions where monopolar RF electrosurgical instrument (40) includes one or more mechanically driven components (e.g., jaws at end effector (46), articulating sections of shaft (44), rotating sections of shaft (44), etc.), body (42) may include various components that are operable to convert one or more mechanical drive inputs from the robotic arm into motion of the one or more mechanically driven components of monopolar RF electrosurgical instrument (40).

As also shown in FIG. 1, body (42) is coupled with a corresponding port (22) of console (20) via a cable (32). Console (20) is operable to provide electrical power to monopolar RF electrosurgical instrument (40) via port (22) and cable (32). In some versions, port (22) is dedicated to driving monopolar RF electrosurgical instruments like monopolar RF electrosurgical instrument (40). In some other versions, port (22) is operable to drive various kinds of instruments (e.g., including instruments (50, 60), etc.). In some such versions, console (20) is operable to automatically detect the kind of instrument (40, 50, 60) that is coupled with port (22) and adjust the power profile to port (22) accordingly. In addition, or in the alternative, console (20) may adjust the power profile to port (22) based on a selection made by an operator via console (20), manually identifying the kind of instrument (40, 50, 60) that is coupled with port (22).

Shaft (44) is operable to support end effector (46) and provides one or more wires or other paths for electrical communication between base (42) and end effector (46). Shaft (44) is thus operable to transmit electrical power from console (20) to end effector (46). Shaft (44) may also include various kinds of mechanically movable components, including but not limited to rotating segments, articulating sections, and/or other kinds of mechanically movable components as will be apparent to those skilled in the art in view of the teachings herein.

End effector (46) of the present example includes an electrode that is operable to apply monopolar RF energy to tissue. Such an electrode may be incorporated into a sharp blade, a needle, a flat surface, some other atraumatic structure, or any other suitable kind of structure as will be apparent to those skilled in the art in view of the teachings herein. End effector (46) may also include various other kinds of components, including but not limited to grasping jaws, etc.

System (10) of this example further includes a ground pad (70) that is coupled with a corresponding port (28) of console (20) via a cable (38). In some versions, ground pad (70) is incorporated into a patch or other structure that is adhered to the skin of the patient (e.g., on the thigh of the patient). In some other versions, ground pad (70) is placed under the patient (e.g., between the patient and the operating table). In either case, ground pad (70) may serve as a return path for monopolar RF energy that is applied to the patient via end effector (46). In some versions, port (28) is a dedicated ground return port. In some other versions, port (28) is a multi-purpose port that is either automatically designated as a ground return port upon console (20) detecting the coupling of ground pad (70) with port (28) or manually designated as a ground return port via an operator using a user input feature of console (20).

Bipolar RF electrosurgical instrument (50) of the present example includes a body (52), a shaft (54) extending distally from body (52), and an end effector (56) at the distal end of shaft (54). Each of these components (52, 54, 56) may be configured and operable in accordance with the above description of corresponding components (42, 44, 46) of monopolar RF electrosurgical instrument (50), except that end effector (56) of this example is operable to apply bipolar RF energy to tissue. Thus, end effector (56) includes at least two electrodes, with those two electrodes being configured to cooperate with each other to apply bipolar RF energy to tissue. Bipolar RF electrosurgical instrument (50) is coupled with console (20) via a cable (34), which is further coupled with a port (24) of console (20). Port (24) may be dedicated to powering bipolar RF electrosurgical instruments. Alternatively, port (24) or may be a multi-purpose port whose output is determined based on either automatic detection of bipolar RF electrosurgical instrument (50) or operator selection via a user input feature of console (20).

Ultrasonic surgical instrument (60) of the present example includes a body (62), a shaft (64) extending distally from body (62), and an end effector (66) at the distal end of shaft (64). Each of these components (62, 64, 66) may be configured and operable in accordance with the above description of corresponding components (42, 44, 46) of monopolar RF electrosurgical instrument (50), except that end effector (66) of this example is operable to apply ultrasonic energy to tissue. Thus, end effector (66) includes an ultrasonic blade or other ultrasonically vibrating element. In addition, base (62) includes an ultrasonic transducer (68) that is operable to generate ultrasonic vibrations in response to electrical power, while shaft (64) includes an acoustic waveguide that is operable to communicate the ultrasonic vibrations from transducer (68) to end effector (66).

Ultrasonic surgical instrument (60) is coupled with console (20) via a cable (36), which is further coupled with a port (26) of console (20). Port (26) may be dedicated to powering ultrasonic electrosurgical instruments. Alternatively, port (26) or may be a multi-purpose port whose output is determined based on either automatic detection of ultrasonic instrument (60) or operator selection via a user input feature of console (20).

While FIG. 1 shows monopolar RF, bipolar RF, and ultrasonic capabilities being provided via three separate, dedicated instruments (40, 50, 60), some versions may include an instrument that is operable to apply two or more of monopolar RF, bipolar RF, or ultrasonic energy to tissue. In other words, two or more of such energy modalities may be incorporated into a single instrument. Examples of how such different modalities may be integrated into a single instrument are described in U.S. Pub. No. 2017/0202591, entitled "Modular Battery Powered Handheld Surgical Instrument with Selective Application of Energy Based on Tissue Characterization," published Jul. 20, 2017, issued as U.S. Pat. No. 11,229,471 on Jan. 25, 2022, the disclosure of which is incorporated by reference herein, in its entirety. Other examples will be apparent to those skilled in the art in view of the teachings herein.

Figure 2:
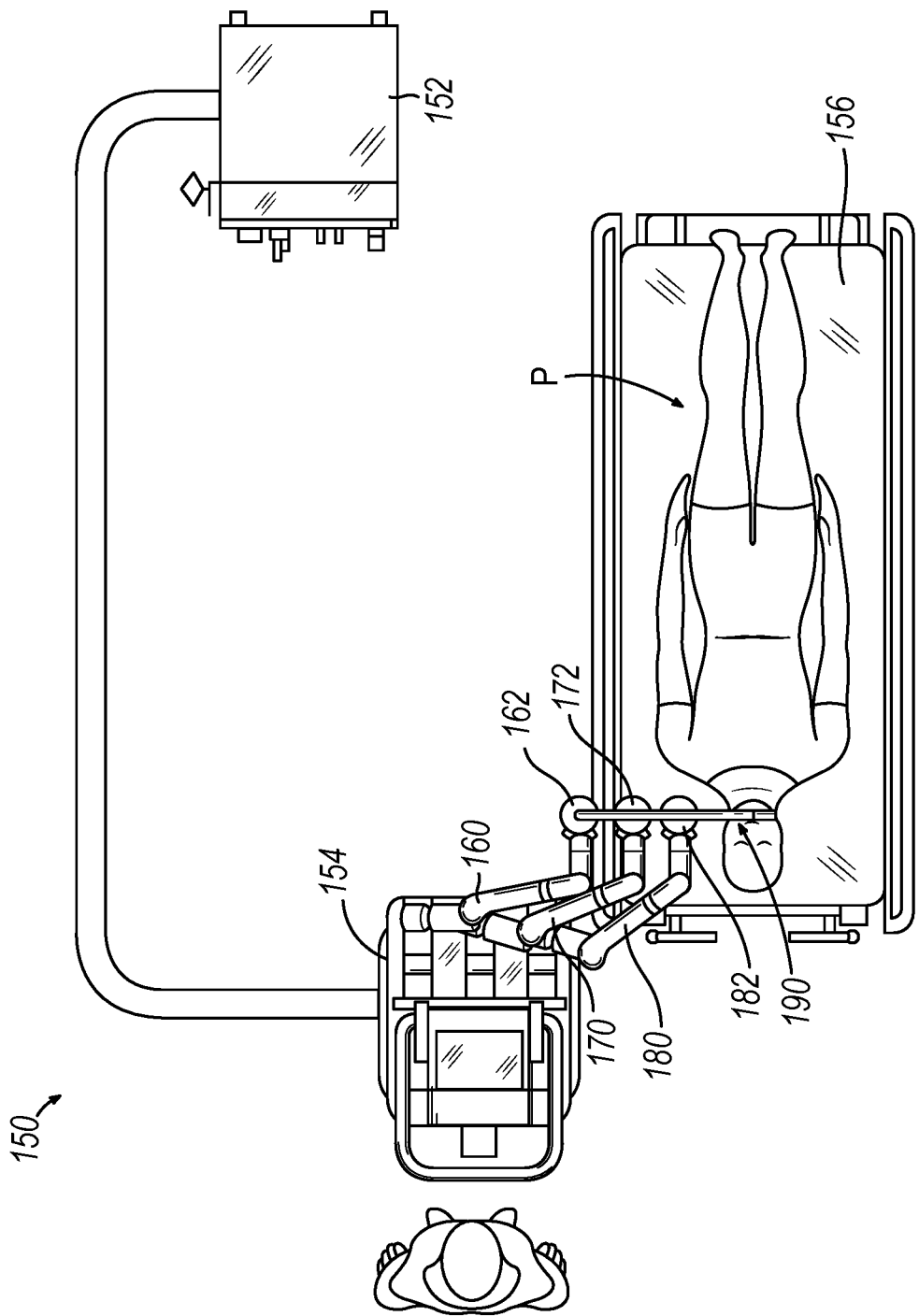
FIG. 2 depicts a schematic view of an example of a robotic surgical system being used in relation to a patient.

FIG. 2 shows an example of a robotic surgical system (150) in relation to a patient (P) on a table (156). System (150) of this example includes a control console (152) and a drive console (154). Console (152) is operable to receive user inputs from an operator; while drive console (154) is operable to convert those user inputs into motion of a set of robotic arms (160, 170, 180). In some versions, consoles (152, 154) collectively form an equivalent to console (20) described above. While consoles (152, 154) are shown as separate units in this example, consoles (152, 154) may in fact be combined as a single unit in some other examples.

Robotic arms (160, 170, 180) extend from drive console (154) in this example. In some other versions, robotic arms (160, 170, 180) are integrated into table (156) or some other structure. Each robotic arm (160, 170, 180) has a corresponding drive interface (162, 172, 182). In this example, three drive interfaces (162, 172, 182) are coupled with one single instrument assembly (190). In some other scenarios, each drive interface (162, 172, 182) is coupled with a separate respective instrument. By way of example only, a drive interface (162, 172, 182) may couple with a body of an instrument, like bodies (42, 52, 62) of instruments (40, 50, 60) described above. In any case, robotic arms (160, 170, 180) may be operable to move instrument (40, 50, 60, 190) in relation to the patient (P) and actuate any mechanically driven components of instrument (40, 50, 60, 190). Robotic arms (160, 170, 180) may also include features that provide a pathway for communication of electrical power to instrument (40, 50, 60, 190). For instance, cables (32, 34, 36) may be at least partially integrated into robotic arms (160, 170, 180). In some other versions, robotic arms (160, 170, 180) may include features to secure but not necessarily integrate cables (32, 34, 36). As yet another variation, cables (32, 34, 36) may simply stay separate from robotic arms (160, 170, 180). Other suitable features and arrangements that may be used to form robotic surgical systems (10, 150) will be apparent to those skilled in the art in view of the teachings herein.

In robotic surgical systems like robotic surgical systems (10, 150), each port (22, 24, 26, 28) may have a plurality of electrical features providing inputs and outputs between console (20, 152) and robotic arms (160, 170, 180) and/or instruments (40, 50, 60, 190). These electrical features may include sockets, pins, contacts, or various other features that are in close proximity with each other. In some scenarios, this proximity may provide a risk of power or signals undesirably crossing from one electrical feature to another electrical feature, which may cause equipment failure, equipment damage, sensor errors, and/or other undesirable results. In addition, or in the alternative, this proximity may provide a risk of generating electrical potentials between proximate components or creating capacitive couplings between electrical features. Such capacitive coupling may provide undesirable results such as power reductions, signal reductions, signal interference, patient injuries, and/or other undesirable results. It may therefore be desirable to provide features to prevent or otherwise address such occurrences at ports (22, 24, 26, 28).

Similarly, each robotic arm (160, 170, 180), each cable (32, 34, 36, 38), and/or each instrument (40, 50, 60, 190) may include a plurality of wires, traces in rigid or flexible circuits, and other electrical features that are in close proximity with each other. Such electrical features may also be in close proximity with other components that are not intended to provide pathways for electrical communication but are nevertheless formed of an electrically conductive material. Such electrically conductive mechanical features may include moving components (e.g., drive cables, drive bands, gears, etc.) or stationary components (e.g., chassis or frame members, etc.). This proximity may provide a risk of power or signals undesirably crossing from one electrical feature to another electrical feature and/or from one electrical feature to an electrically conductive mechanical feature, which may cause equipment failure, equipment damage, sensor errors, and/or other undesirable results. In addition, or in the alternative, this proximity may provide a risk of generating electrical potentials between proximate components or creating capacitive couplings between electrical features and/or between an electrical feature and an electrically conductive mechanical feature. Such capacitive coupling may provide undesirable results such as power reductions, signal reductions, signal interference, patient injuries, and/or other undesirable results. It may therefore be desirable to provide features to prevent or otherwise address such occurrences within robotic arms (160, 170, 180), within cables (32, 34, 36, 38), and/or within instruments (40, 50, 60, 190).

II. Example of Handheld Surgical Instrument

Figure 3:
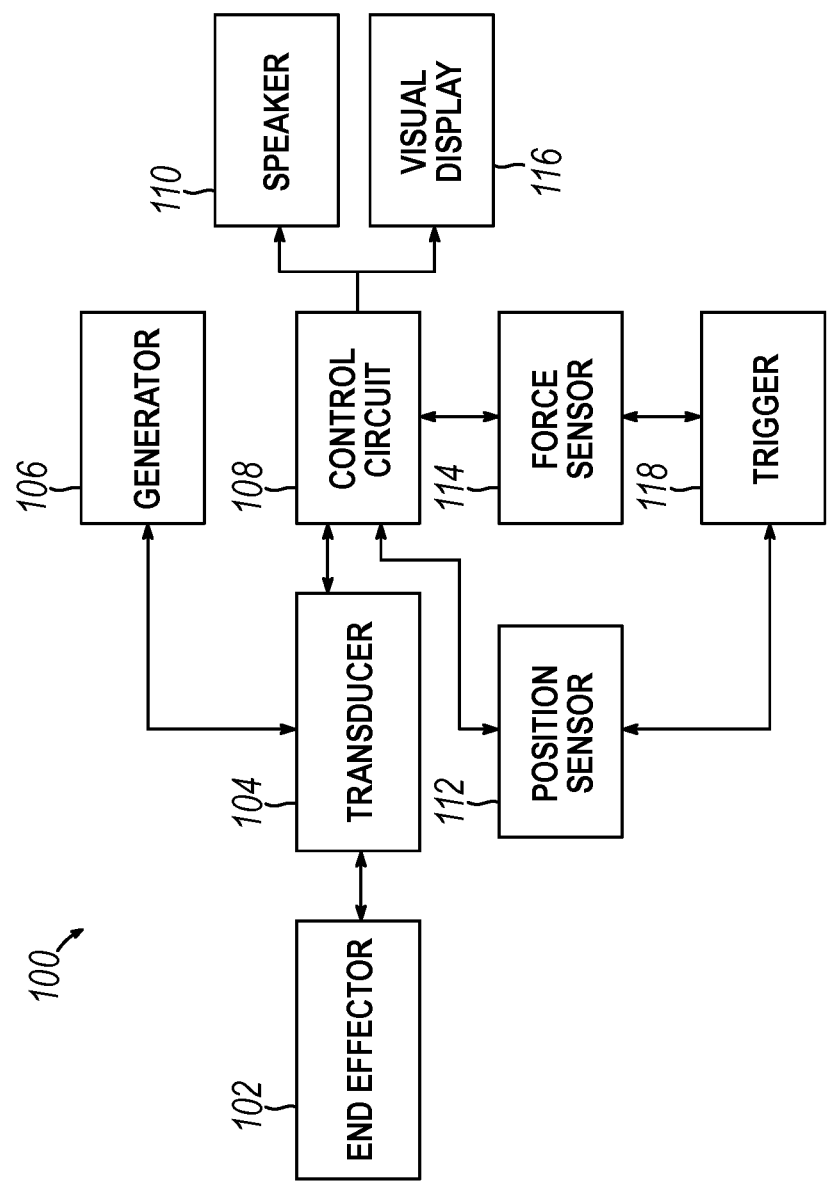
FIG. 3 depicts a schematic view of examples of components that may be incorporated into a surgical instrument.

In some procedures, an operator may prefer to use a handheld surgical instrument in addition to, or in lieu of, using a robotic surgical system (10, 150). FIG. 3 illustrates an example of various components that may be integrated into a handheld surgical instrument (100). In addition to the following teachings, instrument (200) may be constructed and operable in accordance with at least some of the teachings of U.S. Pub. No. 2017/0202608, entitled "Modular Battery Powered Handheld Surgical Instrument Containing Elongated Multi-Layered Shaft," published Jul. 20, 2017, issued as U.S. Pat. No. 10,835,307 on Nov. 11, 2020, the disclosure of which is incorporated by reference herein, in its entirety; and/or various other references cited herein. Instrument (100) of this example includes an end effector (102), an ultrasonic transducer (104), a power generator (106), a control circuit (108), a speaker (110), a position sensor (112), a force sensor (114), a visual display (116), and a trigger (118). In some versions, end effector (102) is disposed at a distal end of a shaft (not shown in FIG. 3), while the other components (104, 106, 108, 110, 112, 114, 116, 118) are incorporated into a handle assembly (not shown in FIG. 3) at the proximal end of the shaft. Some variations may also provide some of components (104, 106, 108, 110, 112, 114, 116, 118) in a separate piece of capital equipment. For instance, power generator (106), speaker (110), and/or visual display (116) may be incorporated into a separate piece of capital equipment that is coupled with instrument (100).

End effector (102) may be configured and operable like end effectors (46, 56, 66) described above, such that end effector (102) may be operable to apply monopolar RF energy, bipolar RF energy, or ultrasonic energy to tissue. Transducer (104) may be configured and operable like transducer (68). Generator (106) may be operable to provide electrical power as needed to drive transducer (68) and/or to provide RF energy via end effector (102). In versions where generator (106) is integrated into a handle assembly of instrument (106), generator (106) may comprise one or more battery cells, etc. Control circuit (108) may include one or more microprocessors and/or various other circuitry components that may be configured to provide signal processing and other electronic aspects of operability of instrument (100). Position sensor (112) may be configured to sense the position and/or orientation of instrument (102). In some versions, control circuit (108) is configured to vary the operability of instrument (102) based on data from position sensor (112). Force sensor (114) is operable to sense one or more force parameters associated with usage of instrument (100). Such force parameters may include force being applied to instrument (100) by the operator, force applied to tissue by end effector (102), or other force parameters as will be apparent to those skilled in the art in view of the teachings herein. In some versions, control circuit (108) is configured to vary the operability of instrument (102) based on data from force sensor (114). In some versions, one or both of sensors (112, 114) may be incorporated into end effector (102). In addition, or in the alternative, one or both of sensors (112, 114) may be incorporated into a shaft assembly (not shown) of instrument (100). Variations of instrument (100) may also incorporate various other kinds of sensors (e.g., in addition to or in lieu of sensors (112, 114) in end effector (102), in the shaft assembly, and/or elsewhere within instrument (100).

Trigger (118) is operable to control an aspect of operation of end effector (102), such as movement of a pivoting jaw, translation of a cutting blade, etc. Speaker (110) and visual display (116) are operable to provide audible and visual feedback to the operator relating to operation of instrument (100). The above-described components (102, 104, 106, 108, 110, 112, 114, 116, 118) of instrument (100) are illustrative examples, such that components (102, 104, 106, 108, 110, 112, 114, 116, 118) may be varied, substituted, supplemented, or omitted as desired.

Figure 4:
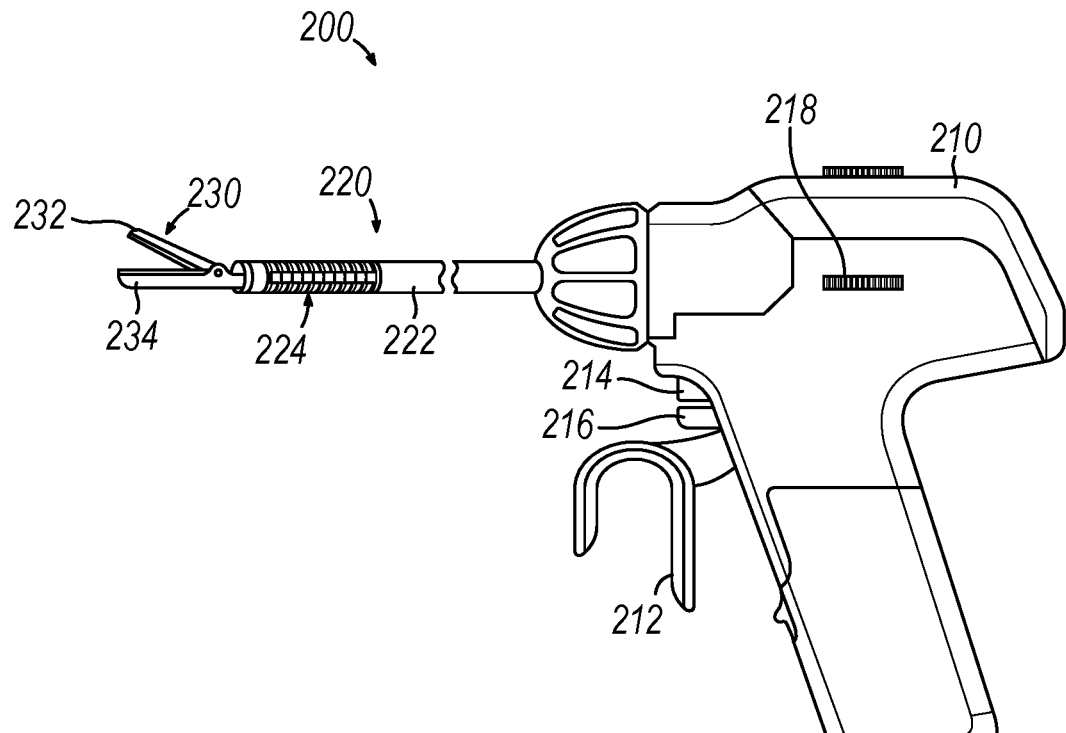
FIG. 4 depicts a side elevation view of an example of a handheld surgical instrument.

FIG. 4 shows an example of a form that instrument (100) may take. In particular, FIG. 4 shows a handheld instrument (200). In addition to the following teachings, instrument (200) may be constructed and operable in accordance with at least some of the teachings of U.S. Pub. No. 2017/0202591, issued as U.S. Pat. No. 11,229,471 on Jan. 25, 2022, the disclosure of which is incorporated by reference herein, in its entirety; and/or various other references cited herein. In the present example, instrument (200) includes a handle assembly (210), a shaft assembly (220), and an end effector (230). Handle assembly (210) includes a pivoting trigger (212), a first trigger button (214), a second trigger button (216), and an articulation control (218). Shaft assembly (220) includes a rigid shaft portion (222) and an articulation section (224). End effector (230) is distal to articulation section (224) and includes an upper jaw (232) and a lower jaw (234).

By way of example only, handle assembly (210) may include one or more of the above-described components (104, 106, 108, 110, 112, 114, 116, 118). Trigger (212) may be operable to drive upper jaw (232) to pivot toward lower jaw (234) (e.g., to grasp tissue between haws (232, 234)). Trigger buttons (214, 216) may be operable to activate delivery of energy (e.g., RF energy and/or ultrasonic energy) via end effector (230). Articulation control (218) is operable to drive deflection of shaft assembly (220) at articulation section (224), thereby driving lateral deflection of end effector (230) away from or toward the central longitudinal axis defined by rigid shaft portion (222). End effector (230) may include one or more electrodes that is/are operable to apply monopolar and/or bipolar RF energy to tissue. In addition, or in the alternative, end effector (230) may include an ultrasonic blade that is operable to apply ultrasonic energy to tissue. In some versions, end effector (230) is operable to apply two or more of monopolar RF energy, bipolar RF energy, or ultrasonic energy to tissue. Other suitable features and functionalities that may be incorporated into end effector (230) will be apparent to those skilled in the art in view of the teachings herein.

Instruments (150, 200) may include a plurality of wires, traces in rigid or flexible circuits, and other electrical features that are in close proximity with each other. Such electrical features may be located within handle assembly (210), within shaft assembly (220), and/or in end effector (230). Such electrical features may also be in close proximity with other components that are not intended to provide pathways for electrical communication but are nevertheless formed of an electrically conductive material. Such electrically conductive mechanical features may include moving components (e.g., drive cables, drive bands, gears, etc.) or stationary components (e.g., chassis or frame members, etc.). This proximity may provide a risk of power or signals undesirably crossing from one electrical feature to another electrical feature and/or from one electrical feature to an electrically conductive mechanical feature, which may cause equipment failure, equipment damage, sensor errors, patient injuries, and/or other undesirable results. In addition, or in the alternative, this proximity may provide a risk of generating electrical potentials between proximate components or creating capacitive couplings between electrical features and/or between an electrical feature and an electrically conductive mechanical feature. Such capacitive coupling may provide undesirable results such as power reductions, signal reductions, signal interference, and/or other undesirable results. It may therefore be desirable to provide features to prevent or otherwise address such occurrences within instruments (150, 200).

III. Further Examples of Surgical Instrument Components

The following description relates to examples of different features that may be incorporated into any of the various instruments (40, 50, 60, 100, 190, 200) described above. While these examples are provided separate from each other, the features described in any of the following examples may be combined with the features described in other examples described below. Thus, the below-described features may be combined in various permutations as will be apparent to those skilled in the art in view of the teachings herein. Similarly, various ways in which the below-described features may be incorporated into any of the various instruments (40, 50, 60, 100, 190, 200) described above will be apparent to those skilled in the art in view of the teachings herein. The below-described features may be incorporated into robotically controlled surgical instruments (40, 50, 60, 190) and/or handheld surgical instruments (100, 200).

A. Example of Ultrasonic End Effector

Figure 5:
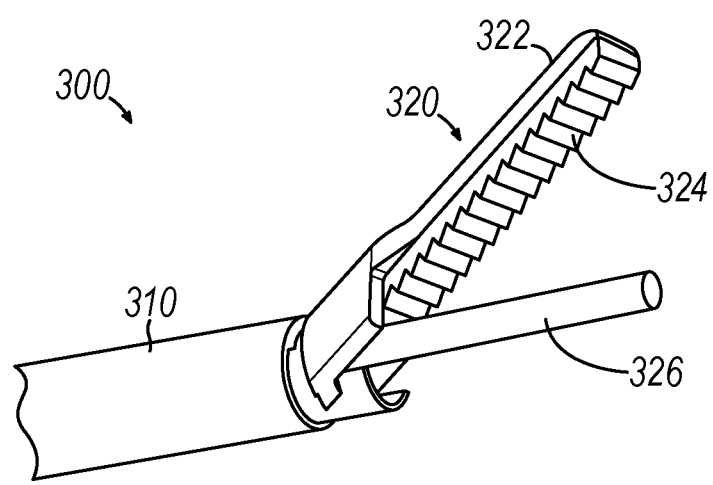
FIG. 5 depicts a perspective view of an example of an end effector that is operable to apply ultrasonic energy to tissue.

FIG. 5 shows a portion of an example of an ultrasonic instrument (300), including a shaft assembly (310) and an end effector (320). End effector (320) includes an upper jaw (322) and an ultrasonic blade (326). Upper jaw (322) is operable to pivot toward ultrasonic blade (326) to thereby compress tissue between a clamp pad (324) of upper jaw (322) and ultrasonic blade (326). When ultrasonic blade (326) is activated with ultrasonic vibrations, ultrasonic blade (326) may sever and seal tissue compressed against clamp pad (324). By way of example only, end effectors (66, 102, 230) may be configured and operable similar to end effector (320).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (300), such risks may occur with respect to an acoustic waveguide in shaft assembly (310) leading to ultrasonic blade (326), as the acoustic waveguide may be formed of an electrically conductive material. In addition, instrument (300) may include one or more sensors in shaft assembly (310) and/or end effector (320); and may also include one or more electrodes and/or other electrical features in end effector (320). Other components of instrument (350) that may present the above-described risks will be apparent to those skilled in the art in view of the teachings herein.

B. Example of Bipolar RF End Effector

Figure 6:
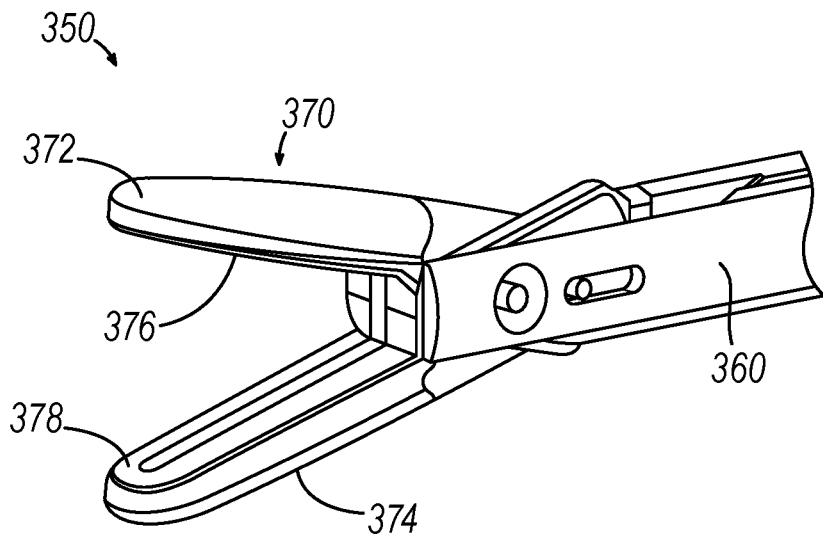
FIG. 6 depicts a perspective view of an example of an end effector that is operable to apply bipolar RF energy to tissue.

FIG. 6 shows a portion of an example of a bipolar RF instrument (350), including a shaft assembly (360) and an end effector (370). End effector (370) includes an upper jaw (372) and a lower jaw (374). Jaws (372, 374) are pivotable toward and away from each other. Upper jaw (372) includes a first electrode surface (376) while lower jaw (374) includes a second electrode surface (378). When tissue is compressed between jaws (372, 374), electrode surfaces (376, 378) may be activated with opposing polarities to thereby apply bipolar RF energy to the tissue. This bipolar RF energy may seal the compressed tissue. In some versions, end effector (370) further includes a translating knife member (not show) that is operable to sever tissue that is compressed between jaws (372, 374). Some variations of end effector (370) may also be operable to cooperate with a ground pad (e.g., ground pad (70)) to apply monopolar RF energy to tissue, such as by only activating one electrode surface (376, 378) or by activating both electrode surfaces (376, 378) at a single polarity. By way of example only, end effectors (64, 102, 230) may be configured and operable similar to end effector (370).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (350), such risks may occur with respect to electrode surface (376, 378) and the wires or other electrical features that extend along shaft assembly (360) to reach electrode surfaces (376, 378). In addition, instrument (350) may include one or more sensors in shaft assembly (360) and/or end effector (370); and may also include one or more electrodes and/or other electrical features in end effector (370). Other components of instrument (350) that may present the above-described risks will be apparent to those skilled in the art in view of the teachings herein.

C. Example of Monopolar Surgical Instrument Features

Figure 7:
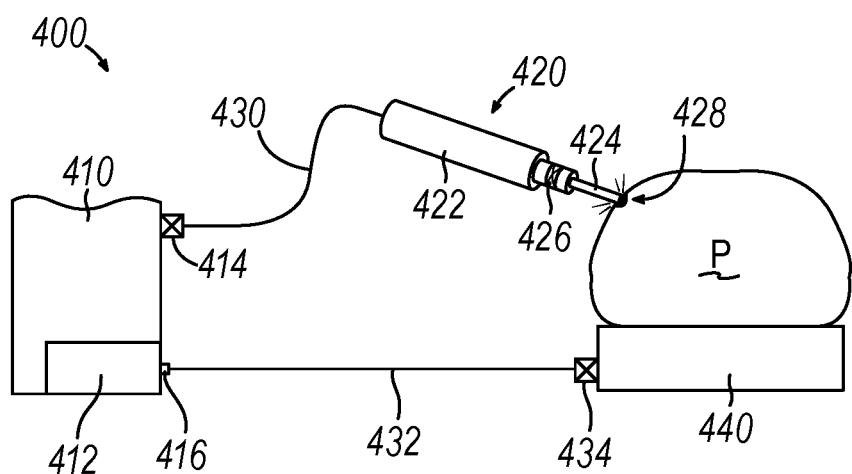
FIG. 7 depicts a schematic view of an example of a surgical instrument that is operable to apply monopolar RF energy to tissue.

FIG. 7 shows an example of a monopolar RF energy delivery system (400) that includes a power generator (410), a delivery instrument (420), and a ground pad assembly (440). In addition to the following teachings, instrument (420) may be constructed and operable in accordance with at least some of the teachings of U.S. Pub. No. 2019/0201077, issued as U.S. Pat. No. 11,291,495 on Apr. 5, 2022, the disclosure of which is incorporated by reference herein, in its entirety; and/or various other references cited herein. Power generator (410) may be operable to deliver monopolar RF energy to instrument (420) via a cable (430), which is coupled with power generator (410) via a port (414). In some versions, port (414) includes an integral sensor. By way of example only, such a sensor in port (414) may be configured to monitor whether excess or inductive energy is radiating from power generator (410) and/or other characteristics of energy being delivered from power generator (410) via port (414). Instrument (420) includes a body (422), a shaft (424), a sensor (426), and a distal electrode (428) that is configured to contact a patient (P) and thereby apply monopolar RF energy to the patient (P). By way of example only, sensor (426) may be configured to monitor whether excess or inductive energy is radiating from instrument (420). Based on signals from sensor (426), a control module in power generator (410) may passively throttle the ground return from ground pad assembly (440) based on data from sensor.

In some versions, ground pad assembly (440) comprises one or more resistive continuity ground pads that provide direct contact between the skin of the patient (P) and one or more metallic components of the ground pad. In some other versions, ground pad assembly (440) comprises a capacitive coupling ground pad that includes a gel material that is interposed between the patient (P) and the ground return plate. In the present example, ground pad assembly (440) is positioned under the patient (P) and is coupled to power generator (410) via a cable (432) via ports (416, 434). Either or both of ports (416, 434) may include an integral sensor. By way of example only, such a sensor in either or both of ports (416, 434) may be configured to monitor whether excess or inductive energy is radiating from ground pad assembly (440).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (420), such risks may occur with respect to sensor (426), distal electrode (428), and/or any other electrical components in instrument (420). Other components of instrument (420) that may present the above-described risks will be apparent to those skilled in the art in view of the teachings herein. Such risks may be greater in versions instrument (420) that are dedicated to providing monopolar RF energy than in the context of bipolar RF instruments such as instrument (350) because a dedicated monopolar RF instrument may lack a ground return path that might otherwise prevent or mitigate the above risks.

D. Example of Articulation Section in Shaft Assembly

Figure 8:
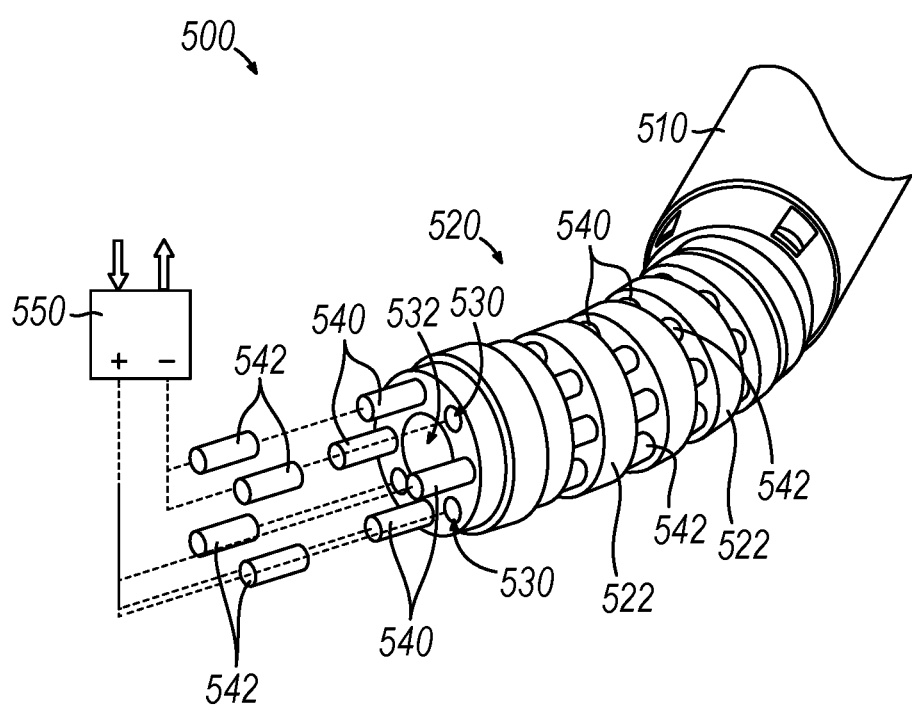
FIG. 8 depicts a perspective view of an example of an articulation section that may be incorporated into a shaft assembly of a surgical instrument.

FIG. 8 illustrates a portion of an instrument (500) that includes a shaft (510) with an articulation section (520). In addition to the following teachings, instrument (500) may be constructed and operable in accordance with at least some of the teachings of U.S. Pub. No. 2017/0202591, issued as U.S. Pat. No. 11,229,471 on Jan. 25, 2022, the disclosure of which is incorporated by reference herein, in its entirety; and/or various other references cited herein. In the present example, an end effector (550) is positioned at the distal end of articulation section (520). Articulation section (520) includes a plurality of segments (522) and is operable to laterally deflect end effector (550) away from and toward the central longitudinal axis of shaft (510). A plurality of wires (540) extend through shaft (510) and along articulation section (520) to reach end effector (550) and thereby deliver electrical power to end effector (550). By way of example only, end effector (550) may be operable to deliver monopolar and/or bipolar RF energy to tissue as described herein. A plurality of push-pull cables (542) also extend through articulation section (520). Push-pull cables (542) may be coupled with an actuator (e.g., similar to articulation control (218)) to drive articulation of articulation section (520). Segments (522) are configured to maintain separation between, and provide structural support to, wires (540) and push-pull cables (542) along the length of articulation section (520). Articulation section (520) of this example also defines a central passageway (532). By way of example only, central passageway (532) may accommodate an acoustic waveguide (e.g., in variations where end effector (550) further includes an ultrasonic blade), may provide a path for fluid communication, or may serve any other suitable purpose. Alternatively, central passageway (532) may be omitted.

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (500), such risks may occur with respect to wires (540) and/or push-pull cables (542). In addition, instrument (500) may include one or more sensors in shaft assembly (510) and/or end effector (550); and may also include one or more electrodes and/or other electrical features in end effector (550). Other components of instrument (500) that may present the above-described risks will be apparent to those skilled in the art in view of the teachings herein.

E. Example of Wiring to End Effector

Figure 9:
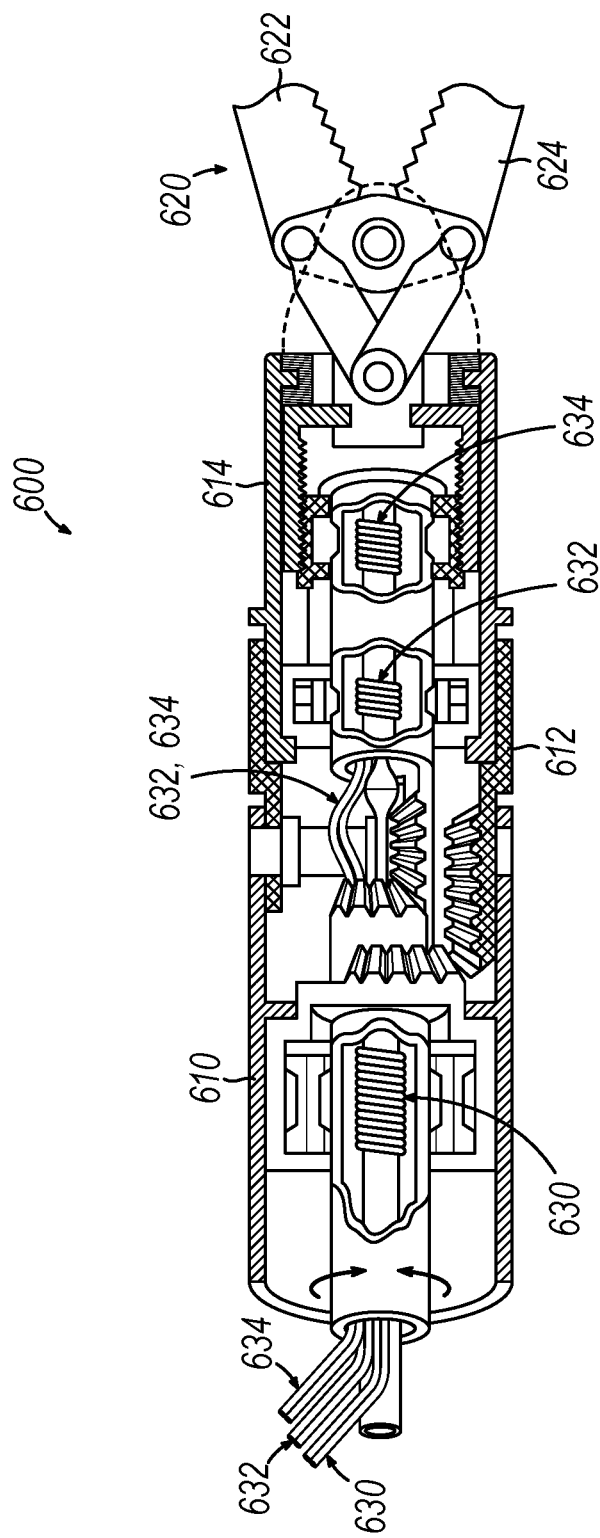
FIG. 9 depicts a side elevation view of a portion of a shaft assembly that may be incorporated into a surgical instrument, with housing components of the shaft being shown in cross-section to reveal internal components of the shaft.

FIG. 9 illustrates a portion of an instrument (600) that includes a shaft (610) with n first articulating segment (612) and a second articulating segment (614). In addition to the following teachings, instrument (600) may be constructed and operable in accordance with at least some of the teachings of U.S. Pub. No. 2017/0202605, entitled "Modular Battery Powered Handheld Surgical Instrument and Methods Therefor," published Jul. 20, 2017, issued as U.S. Pat. No. 10,842,523 on Nov. 24, 2020, the disclosure of which is incorporated by reference herein, in its entirety; and/or various other references cited herein. In the present example, end effector (620) is positioned at the distal end of second articulating segment (614). End effector (620) of this example includes a pair of jaws (622, 624) that are operable to pivot toward and away from each other to grasp tissue. In some versions, one or both of jaws (622, 624) includes one or more electrodes that is/are operable to apply RF energy to tissue as described herein. In addition, or in the alternative, end effector (620) may include an ultrasonic blade and/or various other features. Segments (612, 614) may be operable to pivot relative to shaft (610) and relative to each other to thereby deflect end effector (620) laterally away from or toward the central longitudinal axis of shaft (610).

Instrument (600) of this example further includes a first wire set (630) spanning through shaft (610), a second wire set (632) spanning through shaft (610) and both segments (612, 614), and a third wire set (634) spanning further through shaft (610) and both segments (612, 614). Wire sets (630, 632, 634) may be operable to control movement of segments (612, 614) relative to shaft (610). For instance, power may be communicated along one or more of wire sets (630, 632, 634) to selectively engage or disengage corresponding clutching mechanisms, to thereby allow lateral deflection of one or both of segments (612, 614) relative to shaft (610); and or rotation of one or both of segments (612, 614) relative to shaft (610). Alternatively, power may be communicated along one or more of wire sets (630, 632, 634) to drive corresponding solenoids, motors, or other features to actively drive lateral deflection of one or both of segments (612, 614) relative to shaft (610); and or rotation of one or both of segments (612, 614) relative to shaft (610). In versions where end effector (620) is operable to apply RF energy to tissue, one or more additional wires may extend along shaft (610) and segments (612, 614), in addition to wire sets (630, 632, 634).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (600), such risks may occur with respect to wire sets (630, 632, 634), the electrical components that wire sets (630, 632, 634) are coupled with, and/or other features that drive lateral deflection of one or both of segments (612, 614) relative to shaft (610). In addition, instrument (600) may include one or more sensors in shaft assembly (610) and/or end effector (620); and may also include one or more electrodes and/or other electrical features in end effector (620). Other components of instrument (600) that may present the above-described risks will be apparent to those skilled in the art in view of the teachings herein.

F. Example of Sensors in Shaft Assembly

Figure 10:
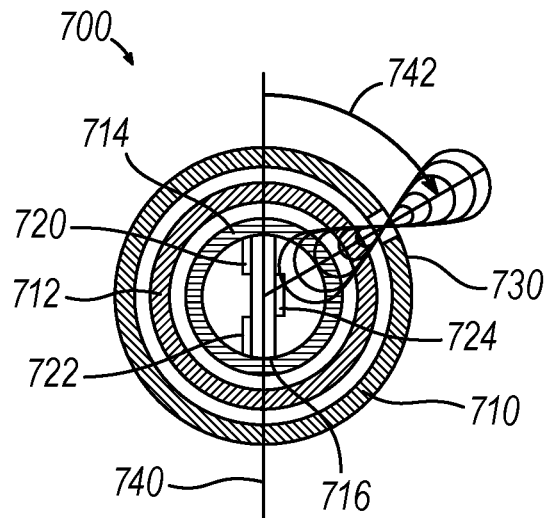
FIG. 10 depicts a cross-sectional end view of another shaft assembly that may be incorporated into a surgical instrument.

FIG. 10 shows an example of another shaft assembly (700) that may be incorporated into any of the various instruments (40, 50, 60, 100, 190, 200, 300, 350, 400, 500, 600) described herein. In addition to the following teachings, shaft assembly (700) may be constructed and operable in accordance with at least some of the teachings of U.S. Pub. No. 2017/0202608, issued as U.S. Pat. No. 10,835,307 on Nov. 17, 2020, the disclosure of which is incorporated by reference herein, in its entirety; and/or various other references cited herein. Shaft assembly (700) of this example includes an outer shaft (710), a first inner shaft (712), and a second inner shaft (714). A support member (716) spans diametrically across the interior of second inner shaft (714). By way of example only, support member (716) may comprise a circuit board, a flex-circuit, and/or various other electrical components. A plurality of sensors (720, 722, 724) are positioned on support member (716) in the present example. A magnet (730) is embedded in outer shaft (710) which is operable to rotate about inner shafts (712, 714).

In some versions, rotation of outer shaft (710) about inner shafts (712, 714) drives rotation of an end effector (not shown), located at the distal end of shaft assembly (700), about a longitudinal axis of shaft assembly (700). In some other versions, rotation of outer shaft (710) about inner shafts (712, 714) drives lateral deflection of the end effector away from or toward the longitudinal axis of shaft assembly (700). Alternatively, rotation of outer shaft (710) about inner shafts (712, 714) may provide any other results. In any case, sensors (720, 722, 724) may be configured to track the position of magnet (730) and thereby determine a rotational position (742) of outer shaft (710) relative to a fixed axis (740). Thus, sensors (720, 722, 724) may collectively serve as a position sensor like position sensor (112) of instrument (100).

Figure 11:
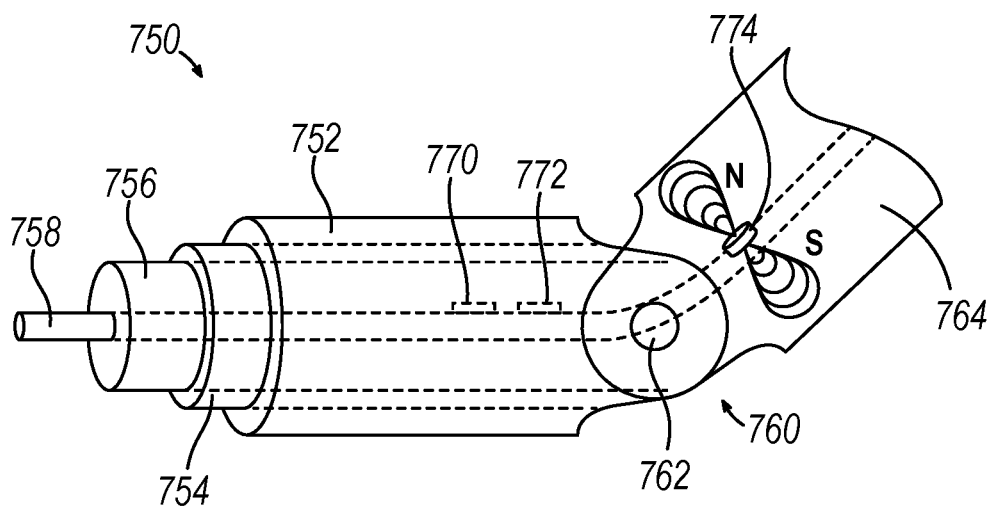
FIG. 11 depicts a schematic view of a portion of another shaft assembly that may be incorporated into a surgical instrument.

FIG. 11 shows an example of another shaft assembly (750) that may be incorporated into any of the various instruments (40, 50, 60, 100, 190, 200, 300, 350, 400, 500, 600) described herein. In addition to the following teachings, shaft assembly (750) may be constructed and operable in accordance with at least some of the teachings of U.S. Pub. No. 2017/0202608, issued as U.S. Pat. No. 10,835,307 on Nov. 17, 2020, the disclosure of which is incorporated by reference herein, in its entirety; and/or various other references cited herein. Shaft assembly (750) of this example includes a plurality of coaxially positioned proximal shaft segments (752, 754, 756) and a distal shaft segment (764). Distal shaft segment (764) is pivotably coupled with proximal shaft segment (752) via a pin (762) to form an articulation joint (760). An end effector (not shown) may be positioned distal to distal shaft segment (764), such that articulation joint (760) may be utilized to deflect the end effector laterally away from or toward a central longitudinal axis defined by proximal shaft segments (752, 754, 756). A flex circuit (758) spans along shaft segments (752, 754, 756, 764) and is operable to flex as shaft assembly (750) bends at articulation joint (760).

A pair of sensors (770, 772) are positioned along flex circuit (758) within the region that is proximal to articulation joint (760); while a magnet (774) is positioned on flex circuit (758) (or elsewhere within distal shaft segment (764)) in the region that is distal to articulation joint (760). Magnet (774) thus moves with distal shaft segment (764) as distal shaft segment (764) pivots relative to proximal shaft segments (752, 754, 756) at articulation joint (760); while sensors (770, 772) remain stationary during such pivoting. Sensors (770, 772) are configured to track the position of magnet (774) and thereby determine a pivotal position of distal shaft segment (764) relative to proximal shaft segments (752, 754, 756). In other words, sensors (770, 772) and magnet (774) cooperate to enable determination of the articulation bend angle formed by shaft assembly (750). Thus, sensors (770, 772) may collectively serve as a position sensor like position sensor (112) of instrument (100).

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instruments (700, 750), such risks may occur with respect to sensors (720, 722, 724, 770, 772), the electrical components that sensors (720, 722, 724, 770, 772) are coupled with, and/or other features within the shaft assemblies of instruments (700, 750). Other components of instruments (700, 750) that may present the above-described risks will be apparent to those skilled in the art in view of the teachings herein.

G. Example of Drive Controls in Body and Shaft Assembly of Instrument

Figure 12:
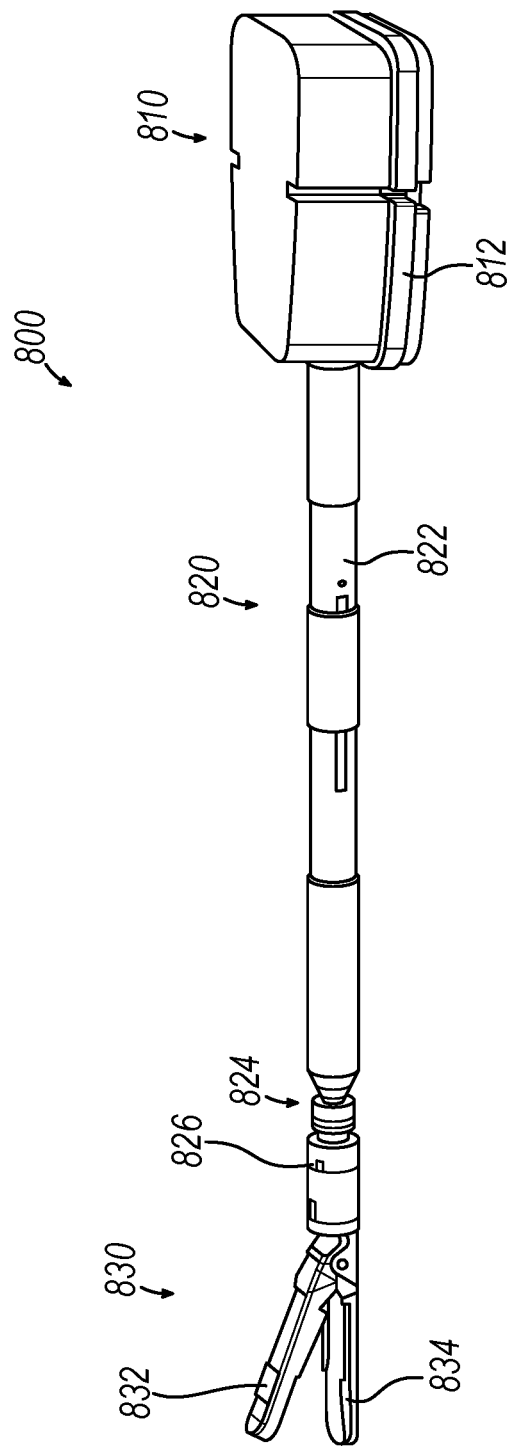
FIG. 12 depicts a perspective view of an example of a surgical instrument that may be incorporated into the robotic surgical system of FIG. 1.
Figure 13:
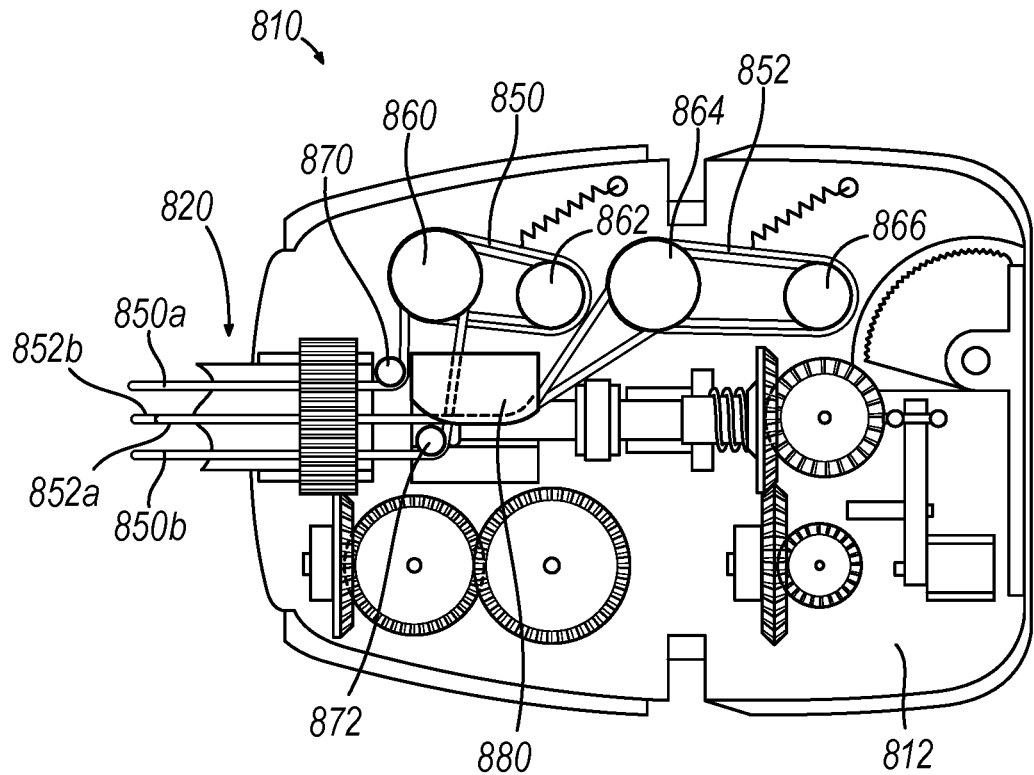
FIG. 13 depicts a top plan view of an interface drive assembly of the instrument of FIG. 12.
Figure 14:
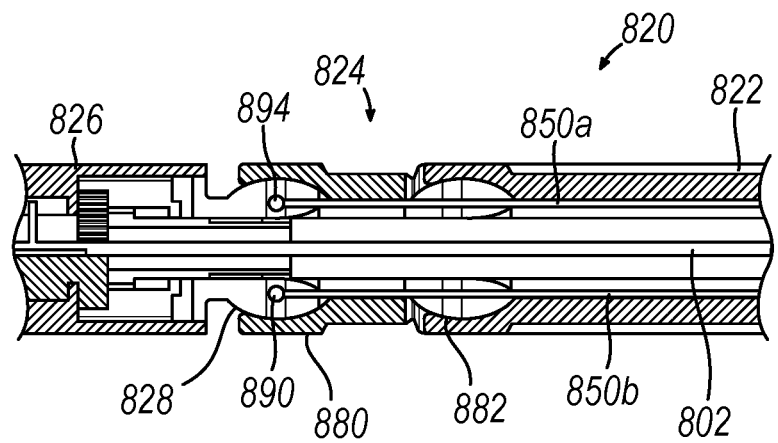
FIG. 14 depicts a cross-sectional side view of an articulation section of a shaft assembly of the instrument of FIG. 12.

FIGS. 12-14 show an example of an instrument (800) that may be incorporated into a robotic surgical system, such as the robotic surgical systems (10, 150) described herein. In addition to the following teachings, instrument (800) may be constructed and operable in accordance with at least some of the teachings of U.S. Pat. No. 9,125,662, the disclosure of which is incorporated by reference herein, in its entirety; and/or various other references cited herein. Instrument (800) of this example includes a body (810), a shaft assembly (820), and an end effector (830). Body (810) includes a base (812) that is configured to couple with a complementary component of a robotic arm (e.g., one of robotic arms (160, 170, 180)). Shaft assembly (820) includes a rigid proximal portion (822), an articulation section (824), and a distal portion (826). End effector (830) is secured to distal portion (826). Articulation section (824) is operable to deflect distal portion (826) and end effector (830) laterally away from and toward the central longitudinal axis defined by proximal portion (822). End effector (830) of this example includes a pair of jaws (832, 834). By way of example only, end effector (830) may be configured and operable like any of the various end effectors (46, 56, 66, 102, 230, 320, 350, 620) described herein.

As shown in FIGS. 13-14, a plurality of drive cables (850, 852) extend from body (810) to articulation section (824) to drive articulation of articulation section (824). Cable (850) is wrapped around a drive pulley (862) and a tensioner (860). Cable (850) further extends around a pair of guides (870, 872), such that cable (850) extends along shaft assembly (820) in two segments (850a, 850b). Cable (852) is wrapped around a drive pulley (866) and a tensioner (864). Cable (852) further extends around a guide (880), such that cable (852) extends along shaft assembly (820) in two segments (852a, 852b). In the present example, each drive pulley (862, 866) is configured to couple with a corresponding drive member (e.g., drive spindle, etc.) of the component of the robotic arm to which base (812) is secured. When drive pulley (862) is rotated, one segment (850a) of cable (850) will translate in a first longitudinal direction along shaft assembly (820); while the other segment (850b) will simultaneously translate in a second (opposite) direction along shaft assembly (820). Similarly, when drive pulley (866) is rotated, one segment (852a) of cable (852) will translate in a first longitudinal direction along shaft assembly (820); while the other segment (852b) will simultaneously translate in a second (opposite) direction along shaft assembly (820).

As shown in FIG. 14, articulation section (824) of the present example includes an intermediate shaft segment (880) that is longitudinally interposed between proximal portion (822) and distal portion (826). A ball feature (828) at the proximal end of distal portion (826) is seated in a socket at the distal end of intermediate shaft segment (880), such that distal portion (826) is operable to pivot relative to intermediate shaft segment (880) along one or more planes. Segments (850a, 850b) of drive cable (850) terminate in corresponding ball-ends (894, 890), which are secured to ball feature (828) of distal portion (822). Drive cable (850) is thus operable to drive pivotal movement of distal portion (826) relative to intermediate shaft segment (880) based on the direction in which drive pulley (862) rotates. A ball feature (882) at the proximal end of intermediate portion (880) is seated in a socket at the distal end of proximal portion (822), such that intermediate portion (880) is operable to pivot relative to proximal portion (822) along one or more planes. In some versions, this pivotal movement of intermediate portion (880) relative to proximal portion (822) is driven by cable (852). As also shown in FIG. 14, an electrical cable (802) passes through articulation section (824). Electrical cable (802) provides a path for electrical communication to end effector (830), thereby allowing for delivery of electrical power (e.g., RF energy) to one or more electrodes in end effector (830), providing a path for electrical signals from one or more sensors in end effector (830) to be communicated back to body (810), and/or other forms of electrical communication.

As noted above, instruments (150, 200) may include electrical features and/or electrically conductive mechanical features that may provide a risk of power or signals undesirably crossing from one electrical feature to another electrical feature and/or from one electrical feature to an electrically conductive mechanical feature. In addition, instruments (150, 200) may include electrical features and/or electrically conductive mechanical features that may provide a risk of generating electrical potentials between proximate components or creating capacitive couplings between electrical features and/or between an electrical feature and an electrically conductive mechanical feature. In the context of instrument (800), such risks may occur with respect to drive cables (850, 852), the components that (850, 852) are coupled with, electrical features within shaft assembly (820), and/or other features within instrument (800). Other components of instrument (800) that may present the above-described risks will be apparent to those skilled in the art in view of the teachings herein.

Figure 15:
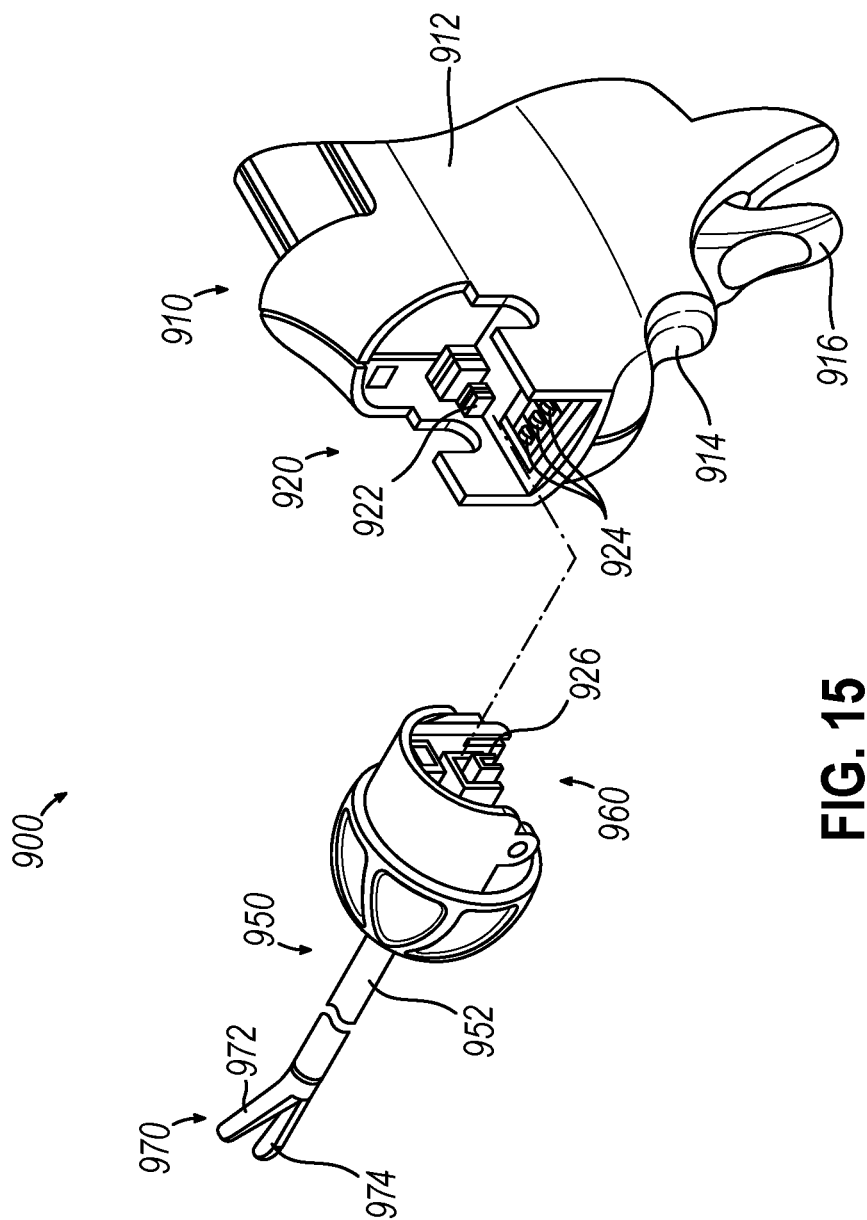
FIG. 15 depicts a perspective view of another example of a handheld surgical instrument, with a modular shaft assembly separated from a handle assembly.

H. Example of Electrical Features at Interface Between Modular Components of Instrument In some instances, it may be desirable to provide a surgical instrument that allows for modular coupling and decoupling of components. For instance, FIG. 15 shows an example of an instrument (900) that includes a handle assembly (910) and a modular shaft assembly (950). While instrument (900) of this example is handheld, similar features and modularity may be readily incorporated into a robotically controlled instrument. Handle assembly (910) of this example includes a body (912), an activation button (914), a pivoting trigger (916), and a shaft interface assembly (920). Shaft interface assembly (920) includes a mechanical drive feature (922) and an array of electrical contacts (924). Electrical contacts (924) may be in electrical communication with a control circuit, power source, and/or various other electrical features within handle assembly (910) as will be apparent to those skilled in the art in view of the teachings herein.

Shaft assembly (950) includes a shaft section (952) and an end effector (970), which includes a pair of jaws (972, 874). Shaft section (952) and end effector (970) may be configured and operable in accordance with any of the various shaft assemblies and end effectors described herein. Shaft assembly (950) of this example further includes a handle interface assembly (960). Handle interface assembly (960) includes a mechanical drive feature (962) and a plurality of electrical contacts (not shown). These electrical contacts of handle interface assembly (960) may be in electrical communication with one or more electrodes, sensors, and/or other electrical components within shaft section (952) and/or end effector (970) as will be apparent to those skilled in the art in view of the teachings herein.

When shaft assembly (950) is coupled with handle assembly (910), mechanical drive feature (922) of handle assembly (910) mechanically couples with mechanical drive feature (962) of shaft assembly (950), such that mechanical drive features (922, 962) may cooperate to communicate motion from a motive power source in handle assembly (910) (e.g., pivoting trigger (916), a motor, etc.) to one or more components within shaft section (952) and, in some versions, end effector (970). In some versions, mechanical drive features (922, 962) cooperate to communicate rotary motion from a motive power source in handle assembly (910) (e.g., pivoting trigger (916), a motor, etc.) to one or more components within shaft section (952) and, in some versions, end effector (970). In addition, or in the alternative, mechanical drive features (922, 962) may cooperate to communicate linear translational motion from a motive power source in handle assembly (910) (e.g., pivoting trigger (916), a motor, etc.) to one or more components within shaft section (952) and, in some versions, end effector (970).

When shaft assembly (950) is coupled with handle assembly (910), electrical contacts (924) of shaft interface assembly (920) also couple with complementary electrical contacts of handle interface assembly (960), such that these contacts establish continuity with each other and thereby enable the communication of electrical power, signals, etc. between handle assembly (910) and shaft assembly (950). In addition to or in lieu of having contacts (924), electrical continuity may be provided between handle assembly (910) and shaft assembly (950) via one or more electrical couplings at mechanical drive features (922, 962). Such electrical couplings may include slip couplings and/or various other kinds of couplings as will be apparent to those skilled in the art in view of the teachings herein.

In some scenarios where electrical power or electrical signals are communicated across mating contacts that provide electrical continuity between two components of an instrument (e.g., contacts (924) of shaft interface assembly (920) and complementary electrical contacts of handle interface assembly (960)), there may be a risk of short circuits forming between such contacts. This may be a particular risk when contacts that are supposed to be electrically isolated from each other are located in close proximity with each other, and the area in which these contacts are located may be exposed to fluids during use of the instrument. Such fluid may create electrical bridges between contacts and/or bleed signals that are being communicated between contacts that are supposed to be coupled with each other. It may therefore be desirable to provide features to prevent or otherwise address such occurrences at contacts of an instrument like instrument (900).

In some scenarios where electrical power or electrical signals are communicated across mechanical couplings between different components of an instrument (e.g., via slip couplings, etc.), such couplings might provide variable electrical resistance in a shaft assembly or other assembly of the instrument. For instance, motion at mechanical drive features (922, 962) may provide variable electrical resistance at an electrical slip coupling between mechanical drive features (922, 962); and this variable electrical resistance may impact the communication of electrical power or electrical signals across the slip coupling. This may in turn result in signal loss or power reductions. It may therefore be desirable to provide features to prevent or otherwise address such occurrences at electrical couplings that are found at mechanical couplings between two moving parts of an instrument like instrument (900).

IV. Examples of Electrical Connector Protection and Monitoring Features

The following description relates to examples of different features that may be incorporated into any of the various surgical systems described above. Thus, the below-described features may be combined in various permutations as will be apparent to those skilled in the art in view of the teachings herein. Similarly, various ways in which the below-described features may be incorporated into any of the various surgical systems described above will be apparent to those skilled in the art in view of the teachings herein. It should be understood that the below-described features may be incorporated into robotically controlled surgical instruments and/or handheld surgical instruments.

As described above in the context of instrument (900) shown in FIG. 15, some instruments may include modular component interfaces, such as shaft interface assembly (920), with a plurality of electrical contacts that are positioned close to each other, such as electrical contacts (924). Such configurations may present a risk of signal cross talk, electrical shorting, or other signal interference from capacitive coupling currents or high voltages occurring across such closely positioned electrical contacts of modular component interfaces. In some scenarios, these issues may be due to a difficulty in providing complete fluid sealing near the electrical connectors and their associated contact arrays. Fluid present at electrical contact interfaces may attenuate transmitted signals or create electrical bridges between contacts that are not intended be bridged. It may therefore be desirable to protect or reinforce the electrical contacts of a modular shaft or end effector from capacitive coupling currents or high voltages; and/or to monitor the electrical contacts and take corrective actions if necessary.

Some instruments include features for protecting electrical connectors or modular components in surgical instruments. Examples of such devices and related concepts are disclosed in U.S. Pat. No. 10,090,616, entitled "Surgical Instrument Handle Assembly with Feature to Clean Electrical Contacts at Modular Shaft Interface," issued Oct. 2, 2018; U.S. Pat. No. 10,813,640, entitled "Method of Coating Slip Rings," issued Oct. 27, 2020; and U.S. Pat. No. 10,639,038, entitled "Staple Cartridge with Short Circuit Prevention Features," issued May 5, 2020, the disclosures of which are incorporated by reference herein, in their entirety. The components and configurations described below may be used in addition to, or in lieu of, the components and configurations described in those patent references.

Figure 16:
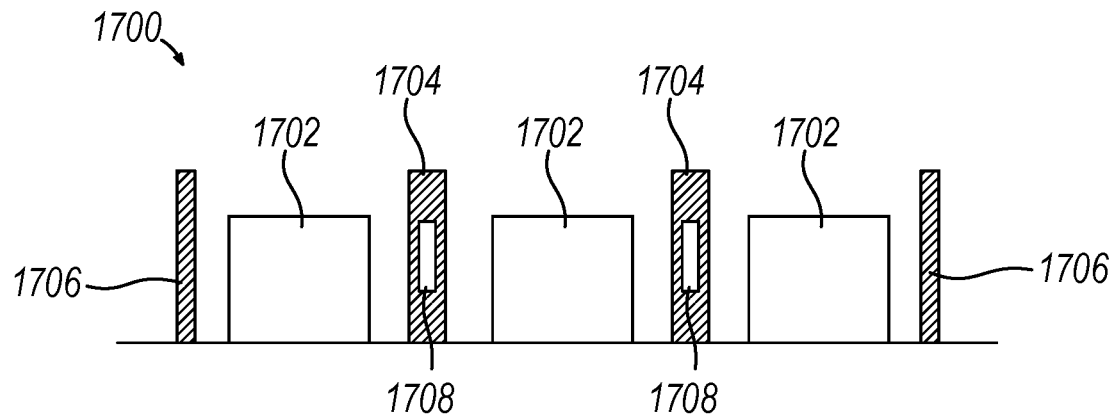
FIG. 16 depicts a schematic view of a first exemplary electrical contact array having a feature for protecting the electrical contacts.

FIG. 16 shows a first contact array (1700) that includes an array of electrical contacts (1702). By way of example only, electrical contacts (1702) may be provided in place of electrical contacts (924) (see, FIG. 15); and may be further configured to function similar to electrical contacts (924) except as described below. Electrical contacts (1702) may further be in electrical communication with a control circuit, power source, and/or various other electrical features within handle assembly (910) (see, FIG. 15) as will be apparent to those skilled in the art in view of the teachings herein.

As shown, contact array (1700) may be surrounded at least on one side, or from both sides of the modular connection, with a grounded, conductive shield (1706) that transfers any externally applied voltages to a return path thereby preventing externally applied voltages from reaching contacts (1702) and any electronics connected to contacts (1702). Shield (1706) is configured to receive a predefined sealing pressure, applied by a feature of handle interface assembly (960) during coupling, ensuring that the outer perimeter of the contact array (1700) is protected and that no gaps in shield (1706) could occur due to interferences or interactions between contact array (1700) and handle interface assembly (960). Therefore, shield (1706) is configured to divert voltage and current away from contacts (1702) and also seal contact array (1700) from invasion of fluids that might otherwise interfere with the electrical connection or result in electrical shorting. In an alternative configuration, rather than providing shield (1706) around contact array (1700), a conductive shield may be disposed around the entire modular connection of the shaft providing a means for the metallic shaft components to have a lower resistance return path connection generally around the modular connection instead of solely around contact array (1700), thereby shielding contacts (1702) from the metallic frame.

In addition to shield (1706), contact array (1700) may also include one or more features (1704) disposed between adjacent contacts (1702). Features (1704) may be formed of a non-conductive material, such as an elastomer, and may be configured to prevent an unwanted electrical bridge (i.e., a short circuit) from forming between two adjacent contacts (1702). More particularly, features (1704) may provide space between contacts (1702) and prevent electrical short circuits even if contact array (1700) is full of fluid, such as by providing a minimum resistance level that is an order of magnitude greater than the contact-to-contact resistance while contaminated with the fluid. In some versions, features (1704) may each include an elastomeric wiper or may be formed with a hydrophobic coating having a high dielectric breakdown and inherent resistance, such as providing a resistance of greater than or equal to 200 ohms between contacts (1702). The sizes and proportions of features (1704) may be configured relative to the proportions and sizes of the contacts (1702), proportionate to the current capacities or resistance of the two contacts (1702), or proportionate to the proximity of features (1704) to the electrical return path and the distance from the conductive shaft components. In some versions, each feature (1704) may be formed having a different size relative to other features (1704). In some versions, as will be described in greater detail below, features (1704) include active electronic controls or sensors (1708) to regulate the signal or power transferred through one or more contacts (1702) by measuring the signal or power via sensor (1708) and providing such measurements to the system console for continued monitoring.

Figure 17:
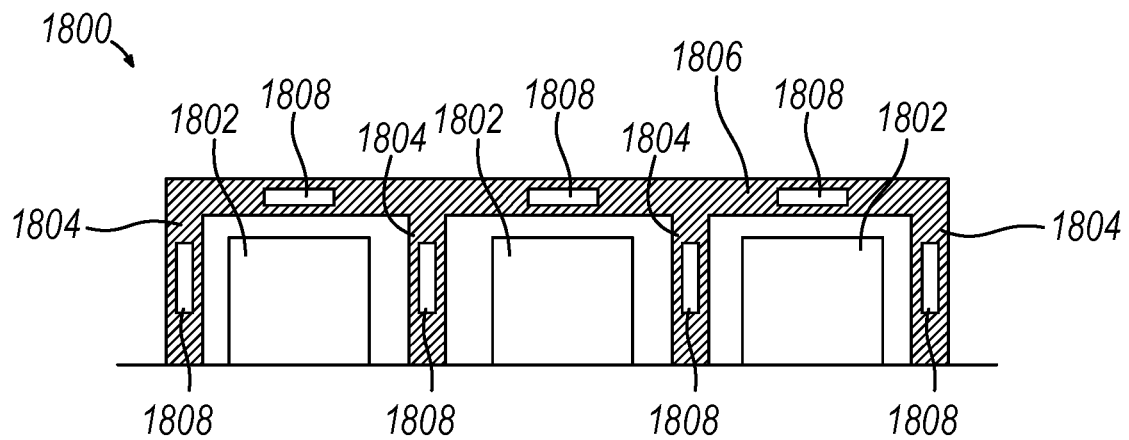
FIG. 17 depicts a schematic view of a second exemplary electrical contact array having a feature for protecting the electrical contacts.

FIG. 17 shows an alternative contact array (1800) for providing substantially the same functionality as contact array (1700) except as described below. Contact array (1800) includes one or more features (1804) disposed between adjacent contacts (1802). Features (1804) may be formed of a non-conductive material, such as an elastomer, and may be configured to prevent an unwanted electrical bridge (i.e., a short circuit) from forming between two adjacent contacts (1802). In some versions, features (1804) may each include an elastomeric wiper or may be formed with a hydrophobic coating having a high dielectric breakdown and inherent resistance. Particularly, features (1804) may be configured with an upper seal or gasket (1806) that spans across each contact (1802). Each contact (1802) is thus configured to be fully encapsulated, upon being electrically connected with the end effector or other modular component, so that no fluid is capable of flowing to or between any two contacts (1802). The encapsulation by features (1804) may nevertheless still allow contacts (1802) to make appropriate electrical contact with corresponding contacts (not shown) in handle interface assembly (960) of shaft assembly (950) when shaft assembly (950) is coupled with handle assembly (910). While not shown, encapsulating features (1804) and seal (1806) may further include a conductive shield disposed on an outer surface relative to contacts (1802), with the conductive shield being configured to transfer electrical voltages and currents to ground, similar to shield (1706) described above. In some versions, as will be described in greater detail below, features (1804) or seals (1806) include active electronic controls or sensors (1808) to regulate the signal or power transferred through one or more contacts (1802) by measuring the signal or power via sensor (1808) and providing such measurements to the system console for continued monitoring.

Figure 18:
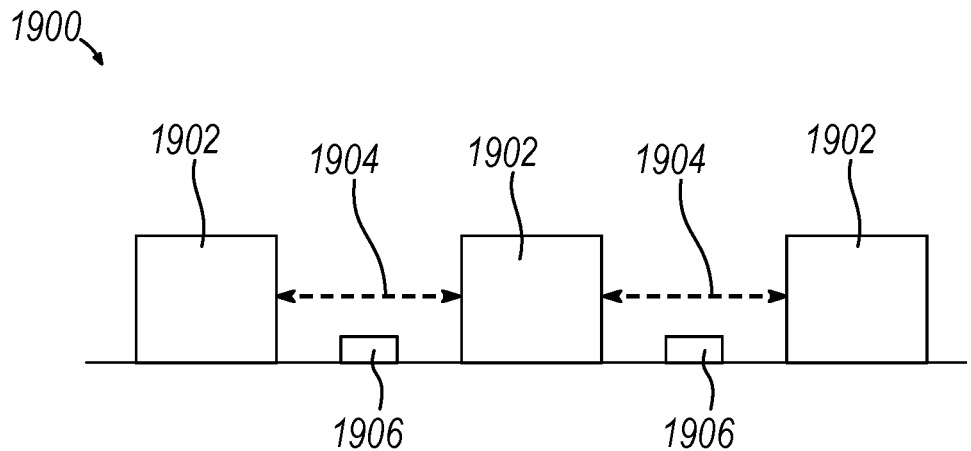
FIG. 18 depicts a schematic view of a third exemplary electrical contact array having a feature for protecting the electrical contacts.

FIG. 18 shows an alternative contact array (1900) for providing substantially the same functionality as contact arrays (1700, 1800) except as described below. Particularly, rather than including features disposed between or around contacts (1902), contacts (1902) may instead be adequately spaced apart to prevent electric voltages or bridges from forming between two contacts (1902). The proportions of the spaces (1904) between contacts (1902) may be configured relative to the proportions and sizes of the contacts (1902) and the voltages configured to transmit across contacts (1902). Alternatively, the proportions of the spaces (1904) between contacts (1902) may be proportionate to the current capacities or resistance of the two contacts (1902). Alternatively, the proportions of the spaces (1904) between contacts (1902) may be or proportionate to the proximity of contacts (1902) to the electrical return path and the distance from the conductive shaft components. In some versions, as will be described in greater detail below, spaces (1904) include active electronic controls or sensors (1906) to regulate the signal or power transferred through one or more contacts (1902) by measuring the signal or power via sensor (1906) and providing such measurements to the system console for continued monitoring.

In addition to the features described above for protecting contact arrays (1700, 1800, 1900), the signals on each contact array (1700, 1800, 1900) may also be actively measured by sensors (1708, 1808, 1906) during operation of the instrument to monitor for aberrant results, with signals indicative of the measurements being sent to the console for monitoring. For example, if a voltage condition above a predefined threshold is detected, the console could take active measures to prevent damage and propagation of the irregular voltage to adjacent contacts. The console may receive voltage or current measurements from each conductive path or trace defined by the contact array (1700, 1800, 1900) and react accordingly to initiate the corrective action. The console may be configured similar to console (20) described above with reference to FIG. 1, and may include a data processor configured and operable to initiate the corrective action, such as adjusting the power profile sent to the end effector. Further, the console may be a component of a robotic electrosurgical system, as described above. Various suitable forms that a console or other control module may take will be apparent to those skilled in the art in view of the teachings herein.

The console may be configured to take any of a plurality of corrective actions if an aberrant voltage or current is measured from a contact array (1700, 1800, 1900) or shield (1706). For example, the console may be configured to automatically apply active voltage clamps, adjust the power output to the end effector, or take other similar protective actions when electrical interference is detected. In some versions, the console may synchronize the voltage clamping with the activation signal for the instrument through a generator or hub interface. The console may also generate a trend line to adjust for the predictive error correction; and in some cases, deactivate RF power from end effector if the console determines that a voltage or current threshold may be reached on the impedance array.

By utilizing the features described above, the instrument may monitor electric potentials at various electrical contacts, slip couplings, or other electrical interface components; and adjust or compensate the power output to the end effector based on any detected losses. For example, the console may direct the generator to increase or decrease the power output; or apply one or more filters to the output signal. As described above, the signals on each contact array (1700, 1800, 1900) or shield (1706) may be actively monitored for aberrant electrical activity to provide active operation data to the console to make such determinations and adjustments in real time.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a shaft assembly; (b) an end effector positioned at a distal end of the shaft assembly, wherein the end effector is operable to engage tissue of a patient; (c) a control module configured to generate a power output to power the end effector; (d) a first electrical connector operatively coupled with the control module, wherein the first electrical connector includes a first plurality of electrical contacts, wherein at least one electrical contact of the first plurality of electrical contacts is configured to transfer the power output to a second plurality of electrical contacts of a second electrical connector while the first and second electrical connectors are coupled; and (e) a plurality of nonconductive structures disposed adjacent each of the plurality of first electrical contacts, wherein the plurality of nonconductive structures are configured to prevent a signal interference between each electrical contact of the first plurality of electrical contacts.

Example 2

The apparatus of Example 1, wherein the plurality of nonconductive structures each includes a sensor, wherein each sensor is configured to measure an electrical signal of an adjacent electrical contact.

Example 3

The apparatus of Example 2, wherein the sensor is configured transmit the measurement of the electrical signal to the control module.

Example 4

The apparatus of Example 3, wherein the control module is configured to: (i) determine whether the electrical signal exceeds a voltage threshold or a current threshold, and (ii) when the electrical signal exceeds a voltage threshold or a current threshold, initiate a corrective action.

Example 5

The apparatus of Example 4, wherein the corrective action includes adjusting the power output.

Example 6

The apparatus of any one or more of Examples 1 through 5, wherein each nonconductive structure of the plurality of nonconductive structures is disposed between two electrical contacts of the first plurality of electrical contacts.

Example 7

The apparatus of any one or more of Examples 1 through 6, wherein each nonconductive structure of the plurality of nonconductive structures is proportionately sized based upon a proximity of the nonconductive structure between the corresponding two electrical contacts of the first plurality of electrical contacts.

Example 8

The apparatus of any one or more of Examples 1 through 7, wherein each nonconductive structure of the plurality of nonconductive structures is proportionately sized based upon a proximity of the nonconductive structure to an electrical ground defined by the power output and upon a proximity of the nonconductive structure to a conductive component of the shaft assembly.

Example 9

The apparatus of Example 8, wherein two nonconductive structures of the plurality of nonconductive structures have sizes that differ from each other.

Example 10

The apparatus of any one or more of Examples 1 through 9, wherein each nonconductive structure of the plurality of nonconductive structures is proportionately sized based upon electrical current capacities of two adjacent electrical contacts of the first plurality of electrical contacts.

Example 11

The apparatus of any one or more of Examples 1 through 10, wherein each nonconductive structure of the plurality of nonconductive structures is proportionately sized based upon an electrical resistance between two adjacent electrical contacts of the first plurality of electrical contacts.

Example 12

The apparatus of any one or more of Examples 1 through 11, wherein each nonconductive structure of the plurality of nonconductive structures provides a resistance of greater than 200 ohms between two adjacent electrical contacts of the first plurality of electrical contacts.

Example 13

The apparatus of any one or more of Examples 1 through 12, wherein the plurality of nonconductive structures are configured to encapsulate each electrical contact of the first plurality of electrical contacts to form a fluid-tight seal.

Example 14

The apparatus of any one or more of Examples 1 through 13, wherein the end effector is operable to receive and apply monopolar RF energy sufficient to cut or seal tissue.

Example 15

The apparatus of any one or more of Examples 1 through 14, wherein the control module is a component of a robotic electrosurgical system.

Example 16

A surgical instrument, comprising: (a) a shaft assembly; (b) an end effector positioned at a distal end of the shaft assembly, wherein the end effector is operable to apply energy to tissue of a patient; (c) a first electrical connector configured to couple with a control module, wherein the first electrical connector includes a first plurality of electrical contacts; (d) a second electrical connector having a second plurality of electrical contacts configured to mate with the first plurality of electrical contacts to form a plurality of conductive bridges, wherein at least one electrical contact of the first plurality of electrical contacts is configured to transfer a power signal to at least one corresponding electrical contact of the second plurality of electrical contacts while the first and second electrical connectors are coupled; and (e) a plurality of nonconductive structures disposed adjacent each electrical bridge of the plurality of electrical bridges, wherein the plurality of nonconductive structures are configured to prevent interference of the power signal between the first plurality of electrical bridges.

Example 17

The apparatus of Example 16, further comprising a body, the shaft assembly being configured to removably couple with the body, the first electrical connector being incorporated into the body, the second electrical connector being incorporated into the shaft assembly.

Example 18

The apparatus of any one or more of Examples 16 through 17, further comprising a conductive shield surrounding the first plurality of electrical contacts, the conductive shield being coupled with ground.

Example 19

The apparatus of Example 18, the conductive shield being further configured to provide a fluid tight seal around the first and second pluralities of electrical contacts while the first and second electrical connectors are coupled.

Example 20

A surgical instrument, comprising: (a) a shaft assembly; (b) an end effector positioned at a distal end of the shaft assembly, wherein the end effector is operable to engage tissue of a patient; (c) a first electrical connector including a first plurality of electrical contacts; and (d) a second electrical connector having a second plurality of electrical contacts configured to mate with the first plurality of electrical contacts to form a plurality of conductive bridges, wherein at least one electrical contact of the first plurality of electrical contacts is configured to transfer a power signal to at least one electrical contact of the second plurality of electrical contacts while the first and second electrical connectors are coupled; wherein each of the plurality of conductive bridges are spaced apart by a distance, wherein the distance is proportionately sized based upon electrical current capacities of two adjacent conductive bridges of the plurality of conductive bridges to prevent signal interference between the two adjacent conductive bridges.

VI. MISCELLANEOUS

Versions of the devices described above may have application in conventional medical treatments and procedures conducted by a medical professional, as well as application in robotic-assisted medical treatments and procedures.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

In addition to the foregoing, the teachings herein may be readily combined with the teachings of U.S. patent application Ser. No. 17/136,137, entitled "Filter for Monopolar Surgical Instrument Energy Path," filed on even date herewith Dec. 29, 2020, published as U.S. Pub. No. 2022/0202474 on Jun. 30, 2022, the disclosure of which is incorporated by reference herein. Various suitable ways in which the teachings herein may be combined with the teachings of U.S. Pub. No. 2022/0202474 will be apparent to those of ordinary skill in the art in view of the teachings herein.

In addition to the foregoing, the teachings herein may be readily combined with the teachings of U.S. patent application Ser. No. 17/136,139, entitled "Electrosurgical Instrument System with Parasitic Energy Loss Monitor," filed on Dec. 29, 2020, published as U.S. Pub. No. 2022/0202470 on Jun. 30, 2022, the disclosure of which is incorporated by reference herein. Various suitable ways in which the teachings herein may be combined with the teachings of U.S. Pub. No. 2022/0202470 will be apparent to those of ordinary skill in the art in view of the teachings herein.

In addition to the foregoing, the teachings herein may be readily combined with the teachings of U.S. patent application Ser. No. 17/136,141, entitled "Energized Surgical Instrument System with Multi-Generator Output Monitoring," filed on Dec. 29, 2020, published as U.S. Pub. No. 2022/0202475 on Jun. 30, 2022, the disclosure of which is incorporated by reference herein. Various suitable ways in which the teachings herein may be combined with the teachings of U.S. Pub. No. 2022/0202475 will be apparent to those of ordinary skill in the art in view of the teachings herein.

In addition to the foregoing, the teachings herein may be readily combined with the teachings of U.S. patent application Ser. No. 17/136,145, entitled "Electrosurgical Instrument with Shaft Voltage Monitor," filed on Dec. 29, 2020, published as U.S. Pub. No. 2022/0202487 on Jun. 30, 2022, the disclosure of which is incorporated by reference herein. Various suitable ways in which the teachings herein may be combined with the teachings of U.S. Pat. App. Pub. No. 2022/0202487 will be apparent to those of ordinary skill in the art in view of the teachings herein.

In addition to the foregoing, the teachings herein may be readily combined with the teachings of U.S. patent application Ser. No. 17/136,154, entitled "Electrosurgical Instrument with Electrical Resistance Monitor at Rotary Coupling," filed on Dec. 29, 2020, published as U.S. Pub. No. 2022/0202476 on Jun. 30, 2022, the disclosure of which is incorporated by reference herein. Various suitable ways in which the teachings herein may be combined with the teachings of U.S. Pub. No. 2022/0202476 will be apparent to those of ordinary skill in the art in view of the teachings herein.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus, comprising:
   (a) a shaft assembly;
   (b) an end effector positioned at a distal end of the shaft assembly, wherein the end effector is operable to engage tissue of a patient;
   (c) a control module configured to generate a power output to power the end effector;
   (d) a first electrical connector operatively coupled with the control module, wherein the first electrical connector includes a first plurality of electrical contacts, wherein at least one electrical contact of the first plurality of electrical contacts is configured to transfer the power output to a second plurality of electrical contacts of a second electrical connector while the first and second electrical connectors are coupled; and
   (e) a plurality of nonconductive structures, wherein each nonconductive structure of the plurality of nonconductive structures is disposed between adjacent electrical contacts of the plurality of first electrical contacts, wherein the plurality of nonconductive structures are configured to prevent a signal interference between each electrical contact of the first plurality of electrical contacts, wherein each nonconductive structure of the plurality of nonconductive structures includes a sensor, such that each sensor is disposed between adjacent electrical contacts of the plurality of first electrical contacts via the corresponding nonconductive structure of the plurality of nonconductive structures.

2. The apparatus of claim 1, wherein each sensor is configured to measure an electrical signal of an adjacent electrical contact.

3. The apparatus of claim 2, wherein the sensor is configured transmit the measurement of the electrical signal to the control module.

4. The apparatus of claim 3, wherein the control module is configured to:
  (i) determine whether the electrical signal exceeds a voltage threshold or a current threshold, and
  ii) when the electrical signal exceeds a voltage threshold or a current threshold, initiate a corrective action.

5. The apparatus of claim 4, wherein the corrective action includes adjusting the power output.

6. The apparatus of claim 1, wherein each nonconductive structure of the plurality of nonconductive structures is proportionately sized based upon a proximity of the nonconductive structure between the corresponding two electrical contacts of the first plurality of electrical contacts.

7. The apparatus of claim 1, wherein each nonconductive structure of the plurality of nonconductive structures is proportionately sized based upon a proximity of the nonconductive structure to an electrical ground defined by the power output and upon a proximity of the nonconductive structure to a conductive component of the shaft assembly.

8. The apparatus of claim 7, wherein two nonconductive structures of the plurality of nonconductive structures have sizes that differ from each other.

9. The apparatus of claim 1, wherein each nonconductive structure of the plurality of nonconductive structures is proportionately sized based upon electrical current capacities of two adjacent electrical contacts of the first plurality of electrical contacts.

10. The apparatus of claim 1, wherein each nonconductive structure of (Original) the plurality of nonconductive structures is proportionately sized based upon an electrical resistance between two adjacent electrical contacts of the first plurality of electrical contacts.

11. The apparatus of claim 1, wherein each nonconductive structure of the plurality of nonconductive structures provides a resistance of greater than 200 ohms between two adjacent electrical contacts of the first plurality of electrical contacts.

12. The apparatus of claim 1, wherein the plurality of nonconductive structures are configured to encapsulate each electrical contact of the first plurality of electrical contacts to form a fluid-tight seal.

13. The apparatus of claim 1, wherein the end effector is operable to receive and apply monopolar RF energy sufficient to cut or seal tissue.

14. The apparatus of claim 1, wherein the control module is a component of a robotic electrosurgical system.

15. A surgical instrument, comprising:
(a) a shaft assembly;
(b) an end effector positioned at a distal end of the shaft assembly, wherein the end effector is operable to engage tissue of a patient;
(c) a first electrical connector including a first plurality of electrical contacts;
(d) a second electrical connector having a second plurality of electrical contacts configured to mate with to form a plurality of conductive bridges, wherein at least one electrical contact of the first plurality of electrical contacts is configured to transfer a power signal to at least one electrical contact of the second plurality of electrical contacts while the first and second electrical connectors are coupled, wherein each of the plurality of conductive bridges are spaced apart by a distance, wherein the distance is proportionately sized based upon electrical current capacities of two adjacent conductive bridges of the plurality of conductive bridges to prevent signal interference between the two adjacent conductive bridges; and
(e) a sensor configured to measure a signal or a power transferred through the first and second electrical connectors, wherein the sensor is positioned in a space defined between adjacent electrical contacts of the first plurality of electrical contacts.

16. An apparatus, comprising:
(a) a shaft assembly;
(b) an end effector positioned at a distal end of the shaft assembly, wherein the end effector is operable to engage tissue of a patient;
(c) a control module configured to generate a power output to power the end effector;
(d) a first electrical connector operatively coupled with the control module, wherein the first electrical connector includes a first plurality of electrical contacts, wherein at least one electrical contact of the first plurality of electrical contacts is configured to transfer the power output to a second plurality of electrical contacts of a second electrical connector while the first and second electrical connectors are coupled; and
(e) a plurality of nonconductive structures disposed adjacent each of the plurality of first electrical contacts, wherein the plurality of nonconductive structures are configured to prevent a signal interference between each electrical contact of the first plurality of electrical contacts, wherein at least a portion of the plurality of nonconductive structures is interposed between the first and second electrical connectors while the first and second electrical connectors are coupled, wherein at least one of the plurality of nonconductive structures includes a sensor configured to measure a signal or a power transferred through the first and second electrical connectors, wherein the sensor is interposed between the first and second electrical connectors while the first and second electrical connectors are coupled.

17. The apparatus of claim 16, wherein the plurality of nonconductive structures are configured to encapsulate each electrical contact of the first plurality of electrical contacts to form a fluid-tight seal.

\* \* \* \* \*